(12) United States Patent
Morita et al.

(10) Patent No.: US 6,575,338 B2
(45) Date of Patent: Jun. 10, 2003

(54) FLUID DISPENSER AND LENS INSPECTION DEVICE

(75) Inventors: Masaya Morita, Kanagawa (JP); Ryo Mori, Kanagawa (JP); Fumio Yuito, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 135 days.

(21) Appl. No.: 09/845,164

(22) Filed: May 1, 2001

(65) Prior Publication Data

US 2001/0035953 A1 Nov. 1, 2001

(30) Foreign Application Priority Data

May 1, 2000 (JP) .......................... 2000-131944
Sep. 14, 2000 (JP) .......................... 2000-279874

(51) Int. Cl.[7] ................................................ G01F 11/04
(52) U.S. Cl. ...................... 222/253; 417/430; 417/410.1
(58) Field of Search ................................ 222/253, 386; 417/430, 410.1

(56) References Cited

U.S. PATENT DOCUMENTS

| | | | | |
|---|---|---|---|---|
| 3,941,517 A | * | 3/1976 | Miyahara | ..................... 417/420 |
| 4,496,245 A | * | 1/1985 | Conrad et al. | ............... 366/143 |
| 4,526,046 A | * | 7/1985 | Oberli | ...................... 73/864.16 |
| 5,393,142 A | * | 2/1995 | Meier | .......................... 366/274 |
| 5,478,149 A | * | 12/1995 | Quigg | ......................... 366/273 |

FOREIGN PATENT DOCUMENTS

| | | | |
|---|---|---|---|
| JP | 8-304052 | 11/1996 | .......... G01B/11/30 |
| JP | 110-146553 | 6/1998 | ............. B05C/5/00 |
| JP | 10-309456 | 11/1998 | ............. B01J/4/00 |

* cited by examiner

Primary Examiner—David A. Scherbel
Assistant Examiner—Melvin A. Cartagena
(74) Attorney, Agent, or Firm—Sughrue Mion, PLLC

(57) ABSTRACT

A fluid dispenser dispenses a fluid alternately from one of a pair of ports (29,31) that are provided on opposite ends of a syringe (26) by moving a piston (42) back and forth inside the syringe. A pair of stirrers (47,48) are provided in the syringe on opposite axial sides of the piston. The stirrers may each individually rotate on an axis that extends in parallel with the moving direction of the piston. A pair of stirrer driving rings (49,50) are mounted on an outer periphery of the syringe in correspondence with the stirrers. Magnets (55,56,59,60) are embedded in the stirrers and the stirrer driving rings such that the stirrer is rotated by magnetic fields that are generated from the stirrer driving ring, as the stirrer driving ring is rotated by a motor (51,52).

13 Claims, 25 Drawing Sheets

FLUID DISPENSER AND LENS INSPECTION DEVICE

BACKGROUND OF THE INVENTION

1. Field of the Invention

The present invention relates to a fluid dispenser that dispenses liquid or fluid from a container, called a syringe, by rising internal pressure of the syringe by a piston. More particularly, the present invention relates to a fluid dispenser for a lubricant containing solid materials, especially for a lubricant sprayed on a reused shutter mechanism before inspecting the shutter speed. The present invention relates also to a lens inspection system, especially for use in recycling reused lenses.

2. Background Arts

An exemplar of a well-known dispenser is disclosed in Japanese Laid-open Patent Application No. 10-309456, that has a syringe partitioned by a piston into two chambers. By driving the piston to reciprocate inside the syringe, a liquid contained in the syringe is dispensed alternately from both chambers. While the liquid is being ejected from one of the chambers, the other chamber is being supplemented with the liquid. Thus, the dispenser of this type can dispense the liquid in continuous succession. Where the liquid to dispense is a lubricant that contains solid components, the lubricant must continually be mixed or agitated for keeping the liquid density constant, because the solid components would otherwise precipitate. For this reason, it is necessary to provide a mixing mechanism in the syringe in that case.

Japanese Laid-open Patent Application No. 10-146553 discloses an adhesive coating apparatus, wherein a mixing device is provided in a syringe for keeping the viscosity of a fluid adhesive material constant. The syringe has an ejection port on the bottom side. The fluid adhesive material is pushed by compressed air toward the ejection port, to be ejected from the ejection port. The mixing device is constituted of an agitating propeller mounted on one end of a drive shaft. The other end of the drive shaft protrudes outside the syringe through a top opening thereof, and is driven to rotate the propeller by an external driving force.

Introducing such a mixing device into the above mentioned dispenser involves a problem that the drive shaft would interfere with a piston rod. To avoid this problem, the drive shaft must be inserted into the syringe through a different position from where the piston rod is inserted. Then a complicated sealing device would be needed for closing a clearance between the drive shaft and the syringe, and thus increases the cost of the dispenser.

SUMMARY OF THE INVENTION

In view of the foregoing, an object of the present invention is to provide a fluid dispenser that can successively dispense a liquid while mixing the liquid continuously in a syringe, has a simple structure and may be manufactured at a low cost.

According to an aspect of the present invention, in a fluid dispenser having a syringe with ports on opposite ends thereof, a piston movable inside said syringe back and forth, and a supply tank being connectable alternately to one of said ports depending upon moving direction of said piston, said fluid dispenser dispensing a fluid from one of said ports that is located on the end of said syringe toward which said piston is moving, while sucking the fluid from said supply tank into said syringe through the other of said ports, the fluid dispenser is characterized by comprising: a pair of stirrers provided respectively in the chambers, the stirrers being rotatable on a rotary axis that extends parallel to the moving direction of the piston; and a pair of stirrer driving devices disposed on an outer periphery of the syringe in correspondence with the stirrers, for driving the stirrers to rotate each individually by a magnetic force.

Since the stirrers are rotated by the magnetic force, there is no problem about the interference of a drive shaft for the stirrer with a piston rod.

The stirrers have the same configuration, and have a plurality of magnets embedded therein symmetrically about the rotary axis of the stirrers, whereas the stirrer driving devices generate magnetic fields that cause the stirrers to rotate. At least one of the stirrers is continuously rotated on one side of the piston, into which the liquid is being sucked.

A piston rod that moves together with the piston extends from opposite end faces of the piston concentrically with the piston and the syringe, and the piston is moved by a piston driving device that is coupled to an end of the piston rod. According to a preferred embodiment, the stirrers are mounted on the piston rod so as to be able to rotate around and slide along the piston rod. In this embodiment, the stirrers are kept in the same axial positions in the syringe by the magnetic forces of the stirrer driving device, even while the piston rod is being moved back and forth together with the piston.

BRIEF DESCRIPTION OF THE DRAWINGS

The above and other objects and advantages of the present invention will become apparent from the following detailed description of the preferred embodiments when read in association with the accompanying drawings, which are given by way of illustration only and thus are not limiting the present invention. In the drawings, like reference numerals designate like or corresponding parts throughout the several views, and wherein.

DETAILED DESCRIPTION OF THE EMBODIMENTS

Figure 1:
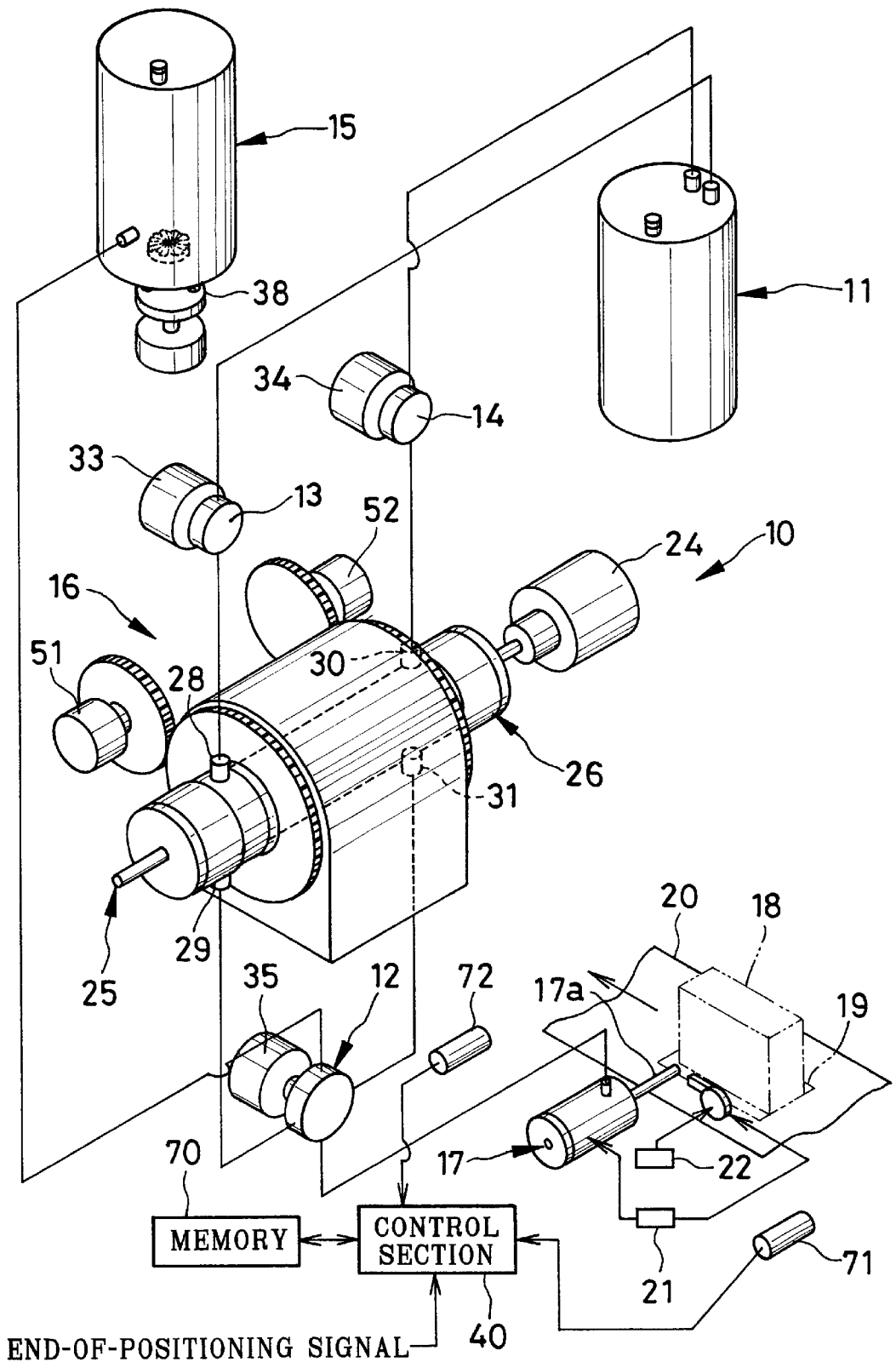
FIG. 1 is a perspective view illustrating essential parts of a lubricant coating system provided with a fluid dispenser according to an embodiment of the present invention.

In FIG. 1, a lubricant coating system 10 is constituted of a collection tank 11, a four-way switching valve 12, two-way switching valves 13 and 14, a supply tank 15, a dispenser 16, a needle valve 17 and other minor elements. The dispenser 16 makes a dispensing operation to put a constant amount of lubricant on an object to coat 18 through the needle valve 17. In this instance, the lubricant is highly volatile and contains solid components.

The object to coat 18 is placed in a predetermined posture on a pallet 19 and conveyed along a conveyer line 20. In a coating station, the pallet 19 is positioned by a positioning device, and the dispenser 16 is activated upon receipt of an end-of-positioning signal from the positioning device, to make the dispensing operation. The needle valve 17 is disposed with its nozzle 17a directed to a coating portion of the object 18. After the coating of the object 18 is finished, the positioning device releases the object upon receipt of an end-of-coating signal, so the coated object 18 is conveyed to the next process, and the object to coat 18 is moved in the coating process.

Figure 2:
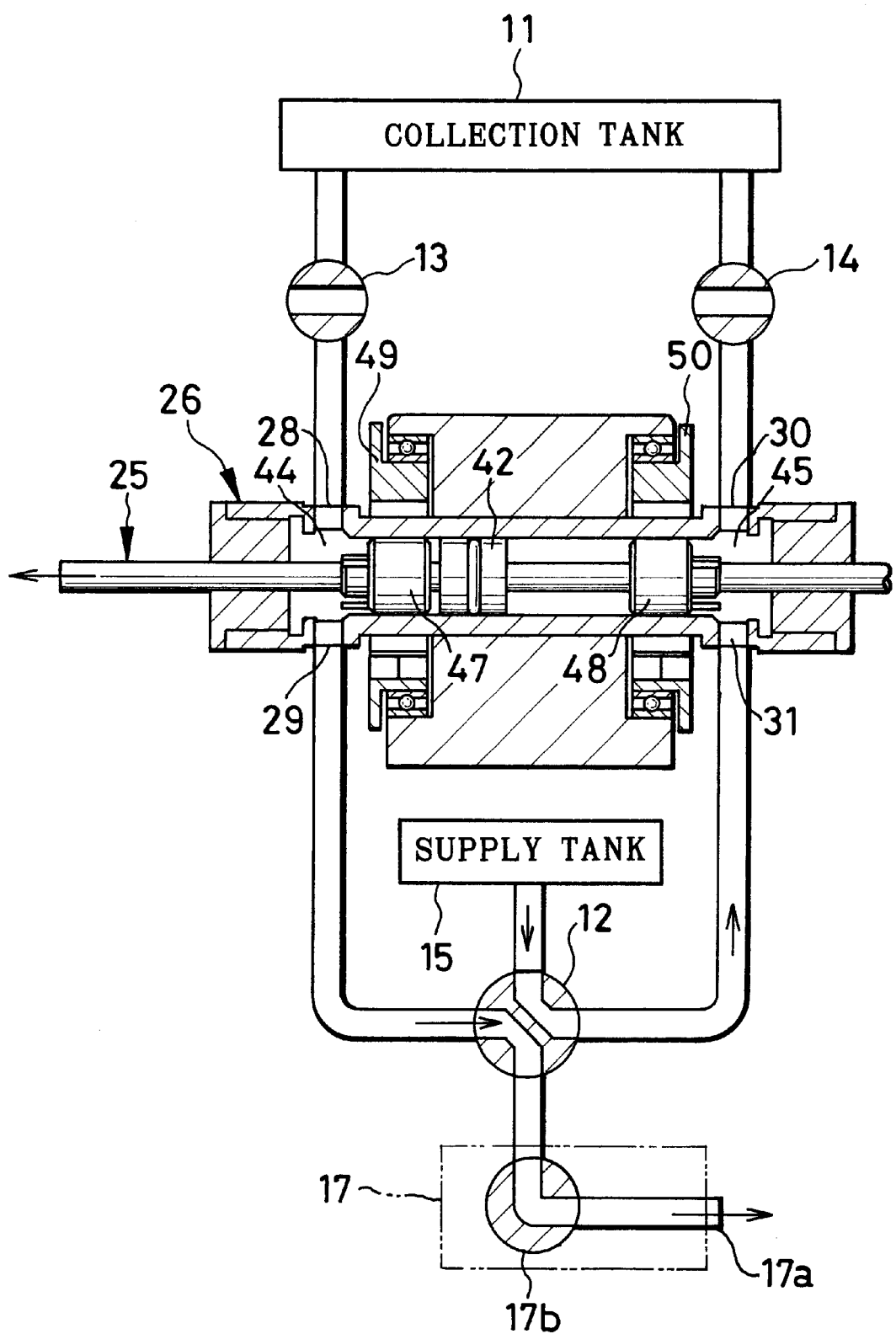
FIG. 2 is an explanatory diagram illustrating the lubricant coating system of FIG. 1 in a position at the end of a forward movement of a piston.

As shown in FIG. 2, the needle valve 17 is provided with a on-off valve 17b for opening and closing the nozzle 17a. The on-off valve 17b is actuated by compressed air that is supplied from a compressor 21. The on-off valve 17b is usually set open. A cleaning mechanism 22 is disposed in the vicinity of the nozzle 17a. The cleaning mechanism 22 uses the compressed air from the compressor 21, for blowing off the lubricant that is stuck to the nozzle 17a.

Referring back to FIG. 1, the dispenser 16 is provided with a rod driving actuator 24, a piston rod 25 and a syringe 26, and controls the amount of movement of the piston rod 25 in one or another direction, to decide the amount of lubricant to be ejected through the needle valve 17. The rod driving actuator 24 consists of a driving device, such as a pulse motor, and a converter that converts a rotary force of the driving device into reciprocation.

As shown in FIG. 2, a piston 42 is securely mounted on the piston rod 25, and is moved back and forth inside the syringe 26, when the piston rod 25 is driven by the rod driving actuator 24. Thus, the rod driving actuator 24 may be called a piston driving device. The syringe 26 is provided with first to fourth ports 28, 29, 30 and 31 that connect the inside of the syringe 26 to the outside. The first and second ports 28 and 29 are located on one side of the piston 42, whereas the third and fourth ports 30 and 31 are located on the other side of the piston 42. The first and third ports 28 and 30 are located on the top side of the syringe 26, whereas the second and fourth ports 29 and 31 are located on the bottom side of the syringe 26 in opposition to the first and third ports 28 and 30 respectively.

The first and third ports 28 and 30 are connected to the two-way switching valves 13 and 14 respectively through Teflon tubes. The two-way switching valves 13 and 14 are connected to the collection tank 11 through Teflon tubes, and are switched over between an open position and a closed position by means of switching actuators 33 and 34 respectively. In the closed position, the two-way switching valves 13 and 14 respectively disconnect the first and third ports 28 and 30 from the collection tank 11. The collection tank 11 is a hermetic tank with a pressure regulation valve, and accepts air bubbles together with the lubricant when they are ejected from the syringe 26 for venting the air out of the syringe 26. Thus, the first and third ports 28 and 30 may be called venting ports.

Figure 3:
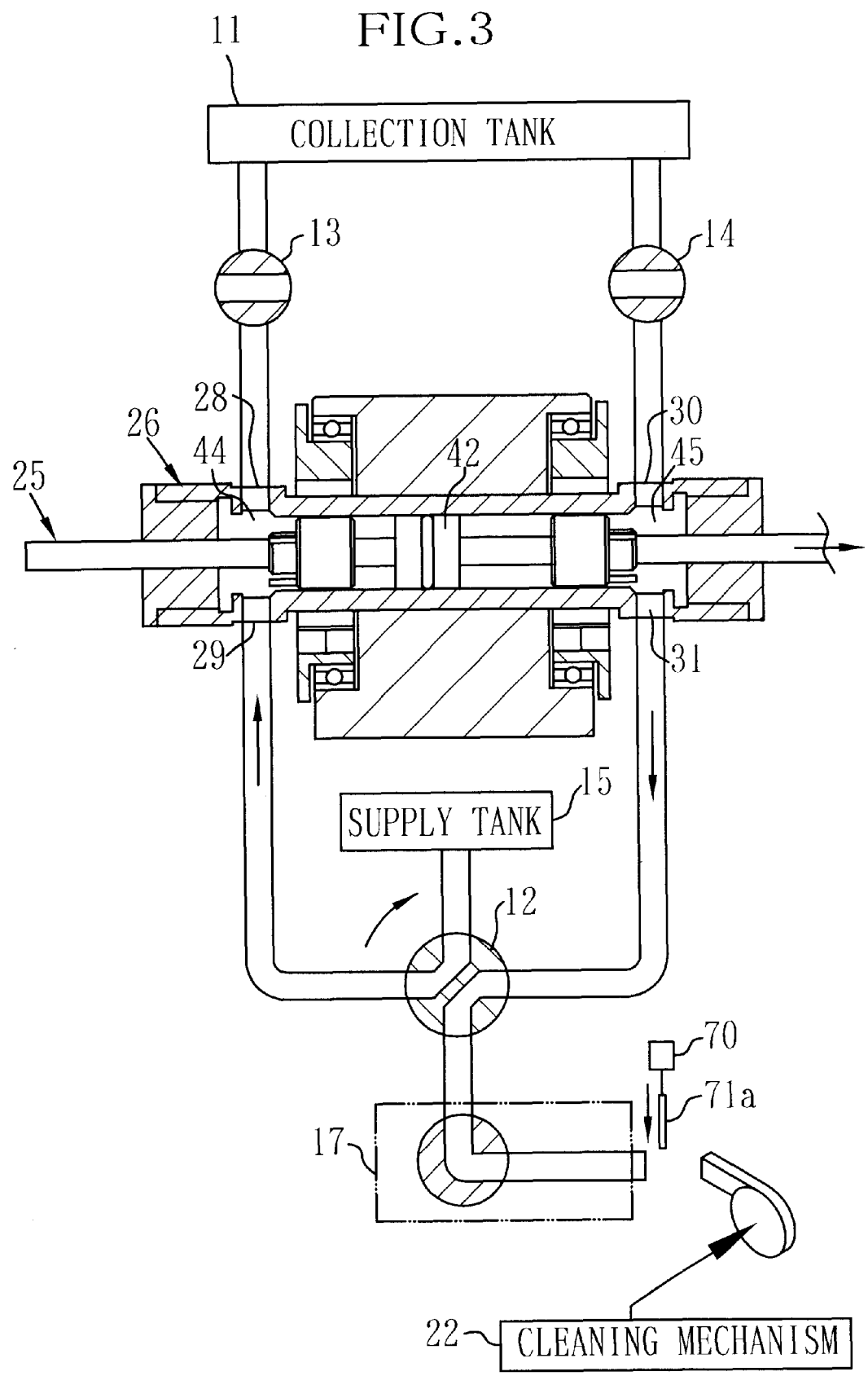
FIG. 3 is an explanatory diagram illustrating the lubricant coating system of FIG. 1 in a position at the start of dispensing operation by a backward movement of the piston.

The second and fourth ports 29 and 31 are connected to the four-way switching valve 12 through Teflon tubes. To the four-way switching valve 12 are also connected the supply tank 15 and the needle valve 17 through Teflon tubes. The four-way switching valve 12 is switched over between a forth movement position as shown in FIG. 2, and a back movement position as shown in FIG. 3. While the piston rod 25 is being moved forward, the four-way switching valve 12 is switched to the forth movement position where the fourth port 31 is connected to the supply tank 15, and the second port 29 is connected to the needle valve 17. While the piston rod 25 is being moved backward, the four-way switching valve 12 is switched to the back movement position, and connects the second port 29 to the supply tank 15 and connects the fourth port 31 to the needle valve 17. The four-way switching valve 12 is switched by driving a four-directional switching actuator 35.

The supply tank 15 is a hermetic tank with a pressure regulation valve, and contains the lubricant. A mixing mechanism 38 is provided inside the supply tank 15, for mixing the lubricant to keep the density of the lubricant constant. The mixing mechanism 38 for the supply tank 15 has a magnet stirrer structure. The above described mechanisms, actuators and other elements are controlled totally by a control section 40. It is to be noted that the Teflon tubes may be replaced by another type of tubes, such as plastic tubes or metal tubes, insofar as the tube material is suitable for the properties of the lubricant. The supply tank 15 is disposed in a higher position than the collection tank 11.

Figure 4:
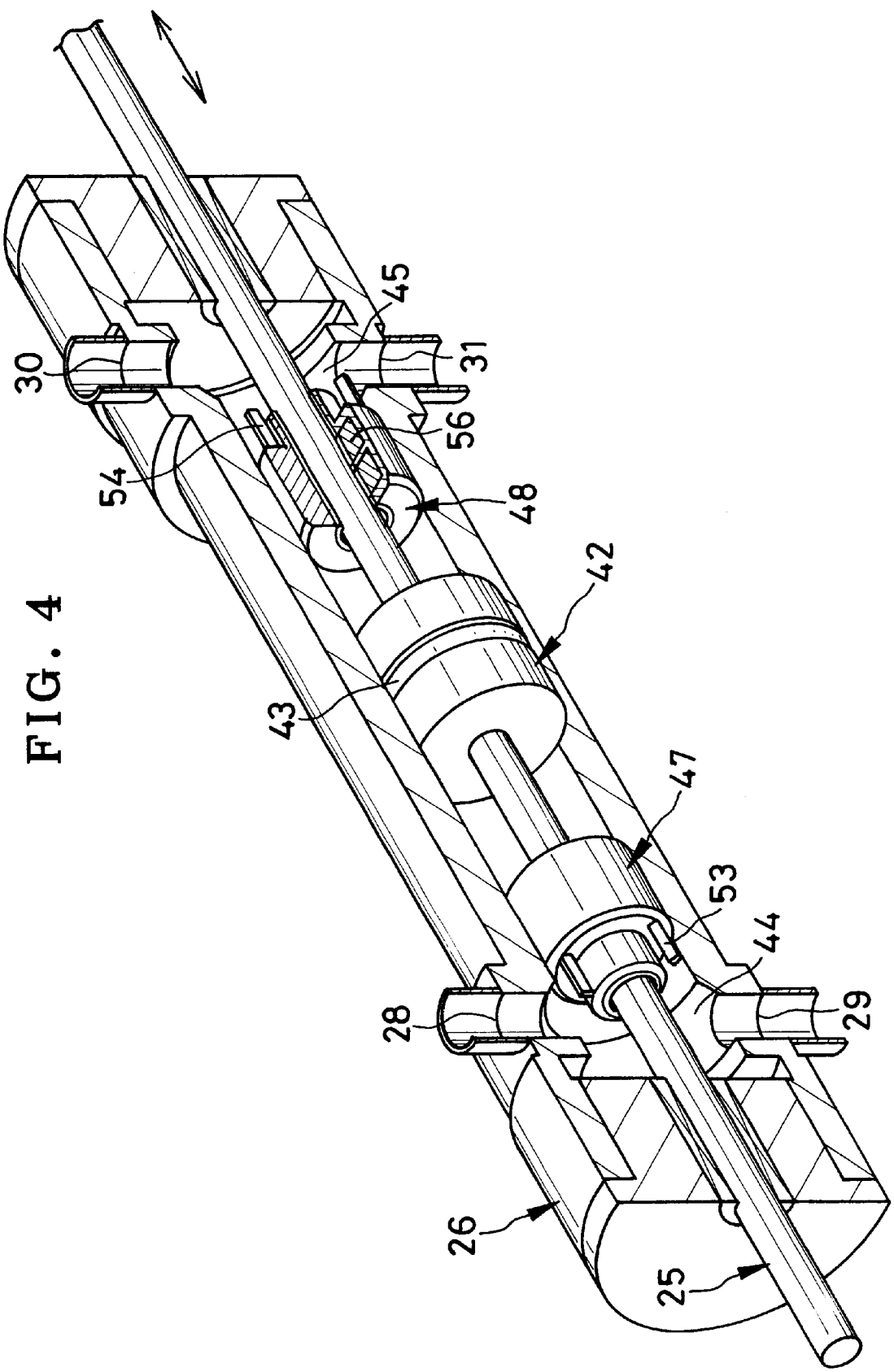
FIG. 4 is a sectional perspective view of the fluid dispenser of FIG. 1.
Figure 5:
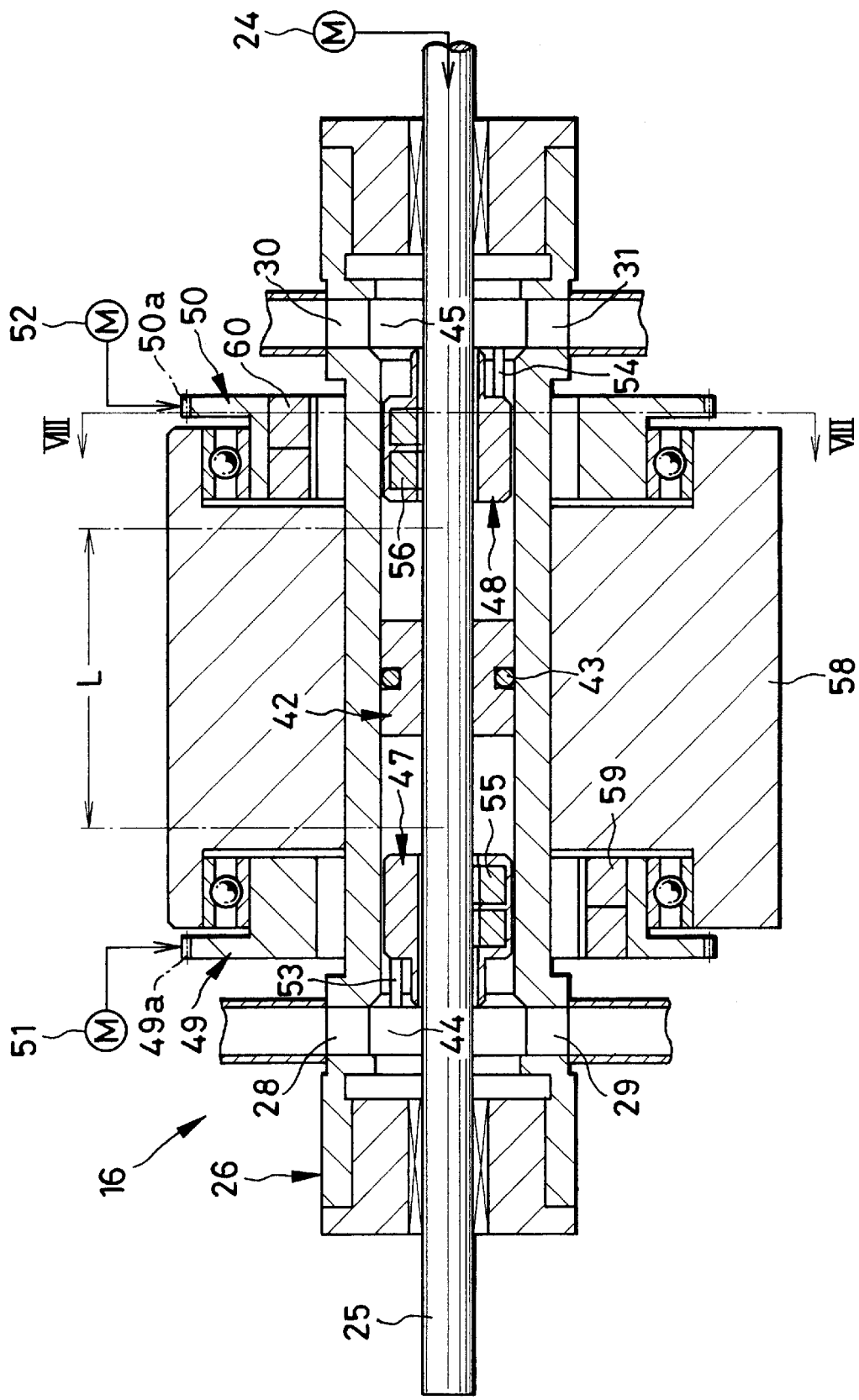
FIG. 5 is a sectional view of the fluid dispenser of FIG. 1.

As shown in FIGS. 4 and 5, the syringe 26 is of a cylindrical shape, and is held horizontal. The syringe 26 has a symmetric internal structure about a center plane including center axes of the cylindrical ports 28 to 31. The syringe 26 has an internal diameter that is approximately equal to an external diameter of the piston 42 at least in a range L in which the piston 42 is moved back and forth. An O-ring 43 is put around the piston 42 at a center position in the axial direction, so as to close the clearance between the outer periphery of the piston 42 and the inner periphery of the syringe 26. Large diameter sections 44 and 45 having a larger diameter than the external diameter of the piston 42 are formed on opposite sides of the piston 42. The large diameter sections 44 and 45 have an axial length that is shorter than the reciprocation range L of the piston 42. The first and second ports 28 and 29 are formed on the top and bottom sides of the large diameter section 44 respectively. The third and fourth ports 30 and 31 are formed on the top and bottom sides of the large diameter sections 45 respectively.

The dispenser 16 is also provided with a mixing mechanism for mixing or stirring the lubricant in the syringe 26, to keep ratio of components constant. The mixing mechanism is constituted of a pair of stirrers 47 and 48, a pair of stirrer drive rings 49 and 50, and a pair of stirring actuators 51 and 52. The stirrers 47 and 48 have the same structure, each having three stirring blades 53 or 54 and internal magnets 55 or 56, as shown in detail in FIGS. 6 and 7. The stirrers 47 and 48 are mounted on the piston rod 25 between the piston 42 and the large diameter sections 44 and 45, such that the stirrers 47 and 48 may rotate around and slide along the piston rod 25 as well. Thus, the piston rod 25 is driven to move the piston 42 back and forth between the stirrers 47 and 48. To avoid wearing the internal periphery of the syringe 26 by friction between the stirrer 47 or 48 and the syringe 26, the stirrers 47 and 48 have a smaller external diameter than the internal diameter of the syringe 26.

The stirrer drive rings 49 and 50 are disposed on the syringe 26 in those positions around the stirrers 47 and 48 respectively, and are mounted through bearings to a syringe holder 58, such that the stirrer drive rings 49 and 50 may rotate around the syringe 26. The stirrer drive rings 49 and 50 are driven to rotate when driving forces are transmitted from the stirring actuators 51 and 52 through gears 49a and 50a that are formed around the outer periphery of the stirrer drive rings 49 and 50 respectively. The stirrer drive rings 49 and 50 have internal magnets 59 or 60, as shown in detail in FIG. 8, so that the stirrer drive rings 49 and 50 hold the stirrers 47 and 48 in those relative positions to the stirrer drive rings 49 and 50, which are determined by the relative positions of the magnets 55 and 56 of the stirrers 47 and 48 to the magnets 59 and 60 of the stirrer drive rings 49 and 50, even while the stirrer drive rings 49 and 50 are rotating. Thus, the stirrers 47 and 48 rotate following the stirrer drive rings 49 and 50.

Figure 6:
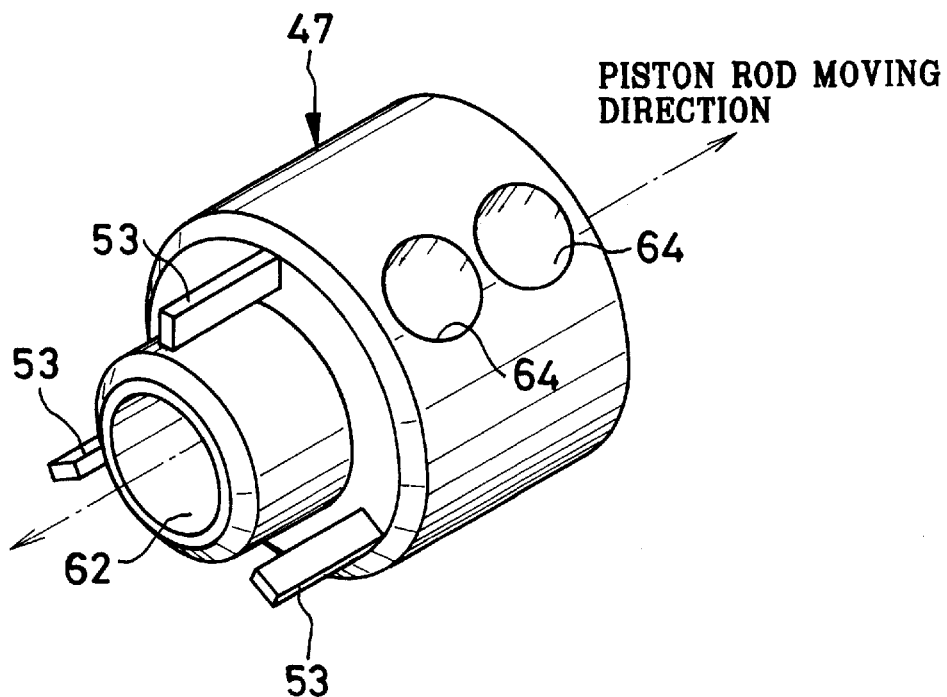
FIG. 6 is a perspective view of a stirrer provided in a syringe of the fluid dispenser.

Referring to FIG. 6, each of the stirrers 47 and 48 has a hole 62 formed through along the axial direction thereof, for putting the piston rod 25 through the hole 62. The stirring blades 53 or 54 are provided on one face end of the stirrers 47 or 48 to protrude in the axial direction of the stirrers 47 or 48, that is, in parallel to the piston rod 25. The three stirring blades 53 or 54 are arranged radially around the hole 62 at intervals of 120°. The stirrers 47 and 48 are mounted on the piston rod 25 in the opposite directions from each other, with their stirring blades 53 and 54 oriented to the large diameter sections 44 and 45 respectively.

Figure 7:
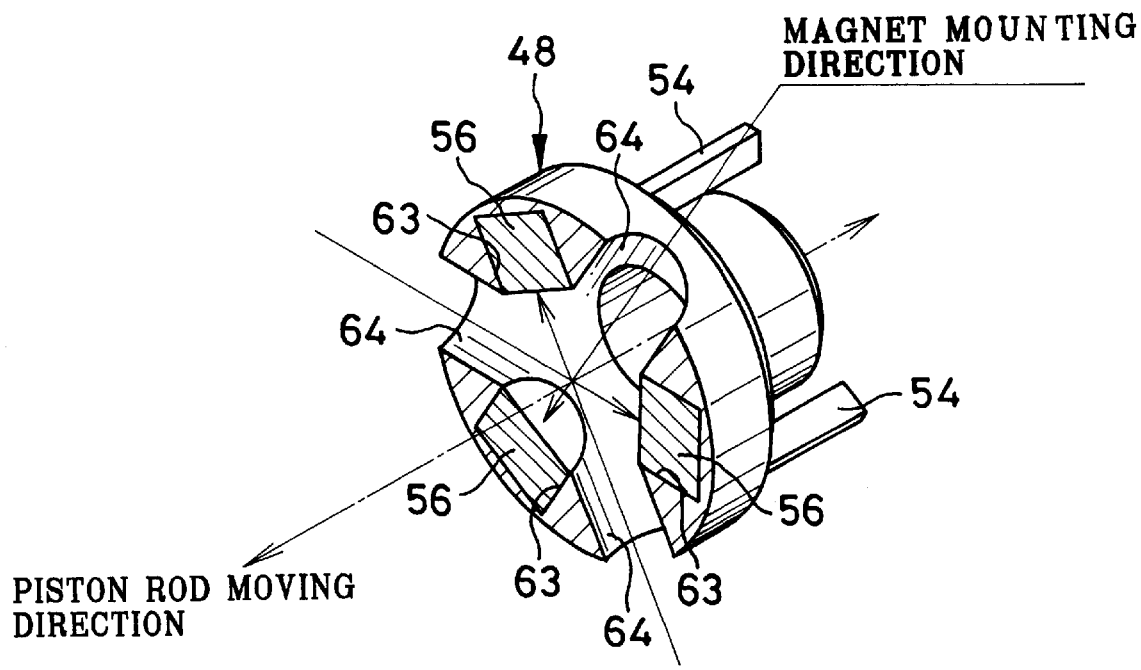
FIG. 7 is a sectional perspective view of the stirrer.

As shown in FIG. 7, the magnets 55 and 56 are embedded in cavities 63 which are formed inside the stirrer 47 or 48 with their open ends oriented toward the center axis of the stirrer 47 or 48. Each stirrer 47 or 48 has six cavities 63, three of which are arranged radially around the center axis at intervals of 120°, and other threes are located on one side of these three cavities in the axial direction of the piston rod 25 in one-to-one alignment with the former three cavities. The magnets 55 and 56 are put into the cavities 63 through holes 64 which are formed through the outer peripheries of the stirrers 47 and 48 in diametrically opposite positions from the cavities 64. The magnets 55 and 56 may be arranged in a different way from illustrated, insofar as they are arranged symmetrical about the rotary axis of the stirrer 47 or 48.

Figure 8:
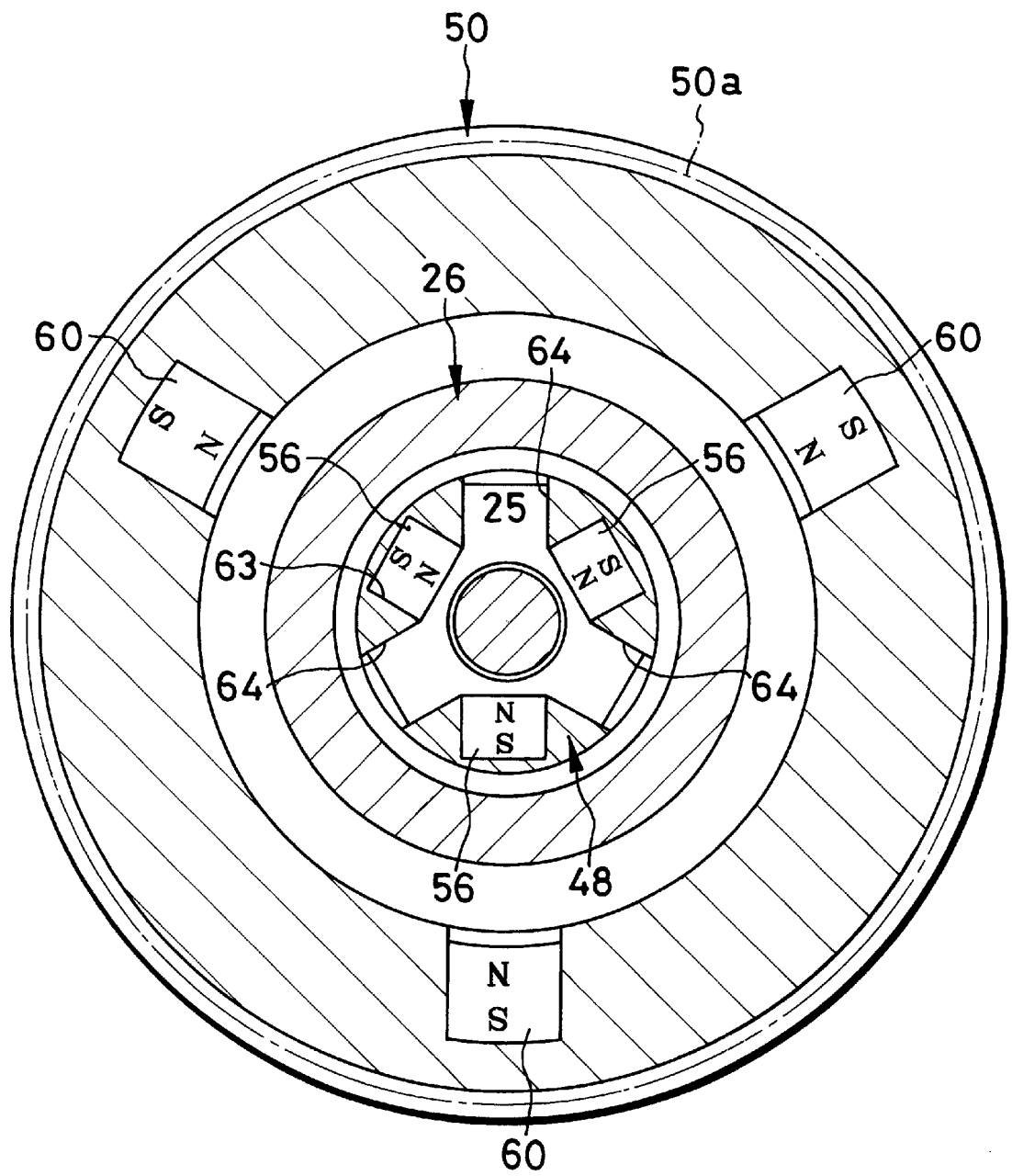
FIG. 8 is a sectional view of the dispenser taken along a line VIII—VIII of FIG. 5.

The stirrer drive rings 49 and 50 have the same structure. As shown in FIG. 8, the magnets 59 and 60 are arranged in correspondence with the magnets 55 and 56 respectively. That is, there are six magnets 59 or 60 in each stirrer drive ring 49 or 50, three of which are arranged radially at intervals of 120°, and other threes are located on one side of these three magnets in the axial direction of the piston rod 25 in one-to-one alignment with the former three magnets. Polarities of the magnets 55, 56, 59 and 60 are so arranged that the magnets 59 attract the magnets 55, whereas the magnets 60 attract the magnets 56. According to this configuration, the stirrer 47 or 48 is held stationary in the stirrer drive ring 49 or 50 while the stirrer drive ring 49 or 50 stops, and rotates along with the stirrer drive ring 49 or 50 as the stirrer drive ring 49 or 50 rotates. It is possible to arrange polarities of the magnets 55, 56, 59 and 60 such that the magnets 55 or 56 repel the magnets 59 or 60 respectively.

Now the operation of the above described lubricant coating system 10 will be briefly described.

Figure 9:
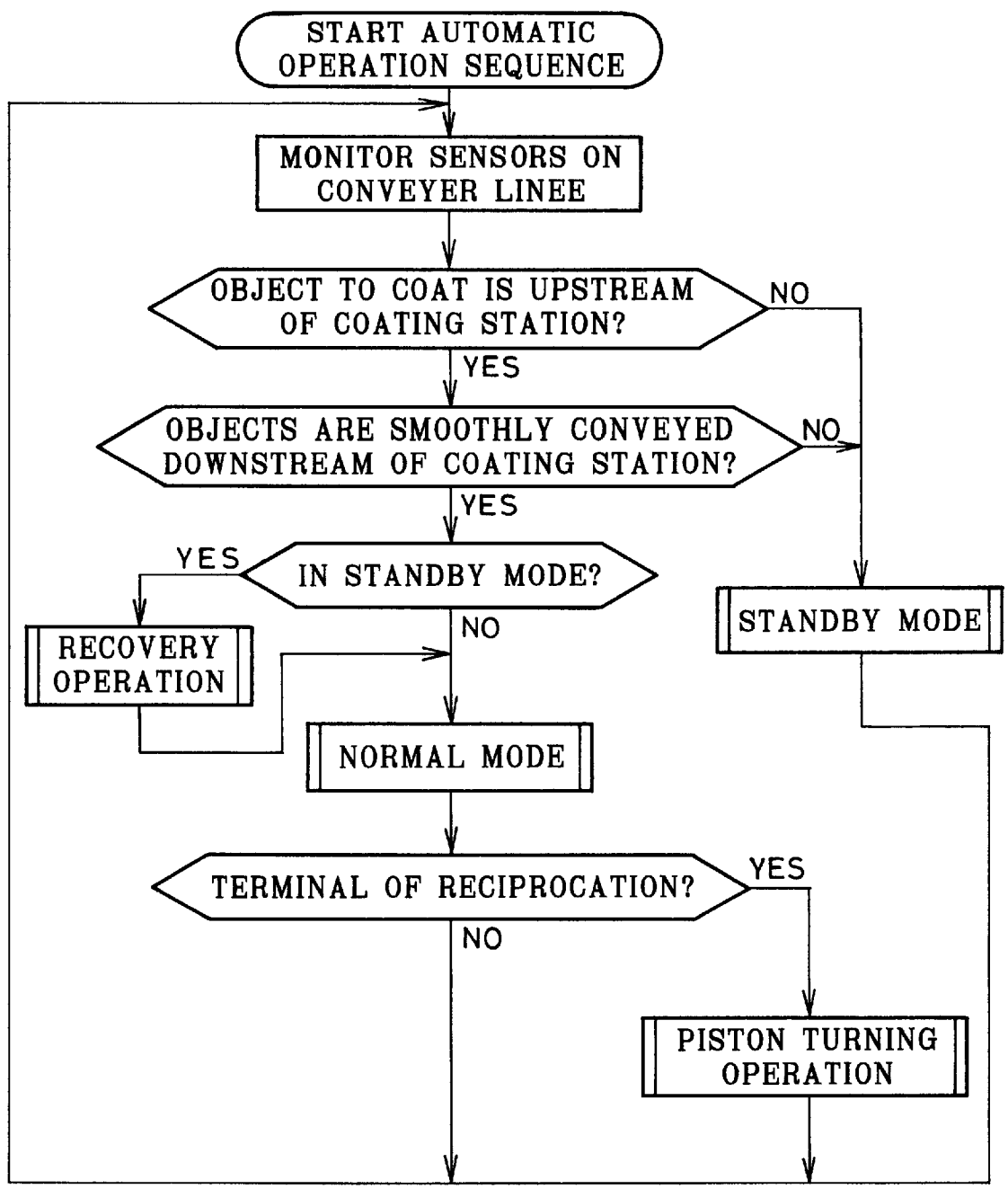
FIG. 9 is a flow chart illustrating an automatic operation sequence of the lubricant coating system.

The lubricant coating system 10 automatically operates according to a sequence stored in a memory 70 (see FIG. 1) of the control section 40. There are a normal mode and a standby mode in the sequence, as shown in FIG. 9, and these modes are automatically switched over appropriately depending upon traffic of the pallets 19 on the conveyer line 20. Specifically, the normal mode is executed when the pallets 19 are successively smoothly conveyed, whereas the standby mode is executed when the pallets 19 on the conveyer line 20 get jammed upstream or downstream of the coating station, or when there are not any pallets 19 upstream the conveyer line 20. Sensors 71 and 72 are disposed in upstream and downstream positions of the coating station, to detect the pallets 19 on the conveyer line 20.

Figure 10:
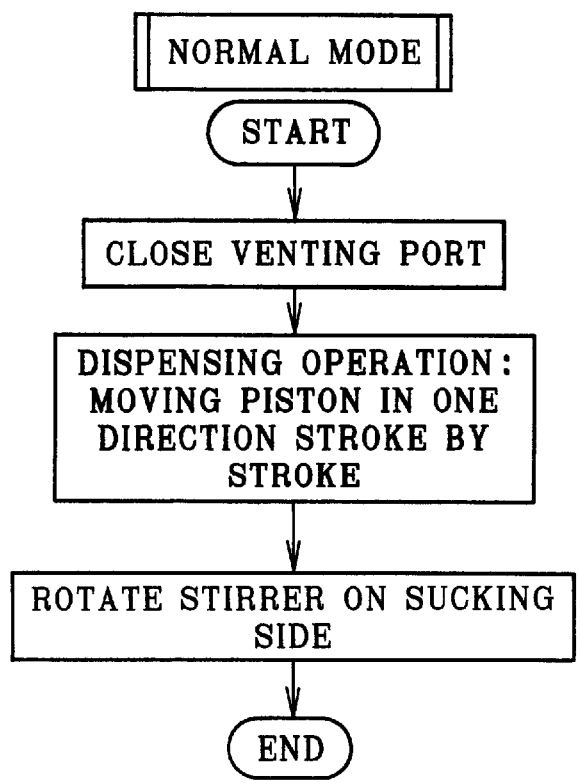
FIG. 10 is a flow chart illustrating a sequence of a normal mode of the lubricant coating system.

In the normal mode, the dispensing operation is performed while setting the on-off valve 17b of the needle valve 17 open. As shown in FIG. 10, at the start of the normal mode, it is checked whether the two-way switching valves 13 and 14 are set in the closed position, and if not, the valves 13 and 14 are switched to the closed position. Although it is not shown in the drawings, the position of the four-way switching valve 12 is also checked to confirm that the switching valve 12 is set in either the forth movement position or the back movement position.

Thereafter, upon receipt of the end-of-positioning signal, the rod driving actuator 24 is driven to move the piston rod 25 in one direction by a constant stroke. Then, a corresponding amount of lubricant is ejected through the needle valve 17, and is put on the object to coat 18. One of the stirrers 47 and 48 that is placed in the sucking side of the syringe 26, e.g. the stirrer 48 in the forth movement of the piston rod 25, is always rotated, whereas the other stirrer in the ejection side of the syringe 26 is not rotated. Because the stirrers 47 and 48 can slide on the piston rod 25, the stirrers 47 and 48 are held in the same relative positions to the stirrer drive rings 49 and 50 by virtue of the magnets 55, 56, 59 and 60, even while the piston rod 25 is moved in the axial direction.

Figure 11:
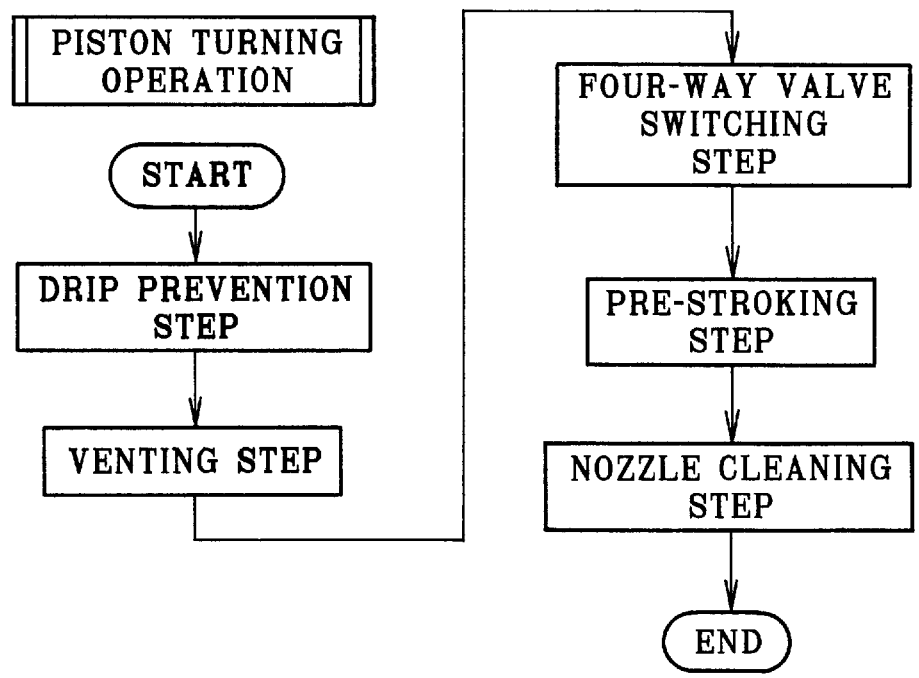
FIG. 11 is a flow chart illustrating a piston turning operation of the lubricant coating system.

The rod driving actuator 24 drives the piston rod 25 to move in one direction by one stroke each time it receives the end-of-positioning signal, to coat the object 18 with the constant amount of lubricant. When the piston rod 25 reaches a terminal of one moving direction, the control section 40 controls the rod driving actuator 24 to change the moving direction of the piston rod 25. Correspondingly, the sucking side and the ejecting side of the syringe 26 are exchanged, and the stirrer 47 or 48 that has been rotating stops rotating, and the other stirrer 47 or 48 starts rotating continually Before starting the dispensing operation in the opposite direction, a piston turning operation is executed. As shown in FIG. 11, the piston turning operation consists of a drip prevention step, a venting step, a valve switching step for the four-way valve 12, a pre-stroking step, and a nozzle cleaning step.

Figure 12:
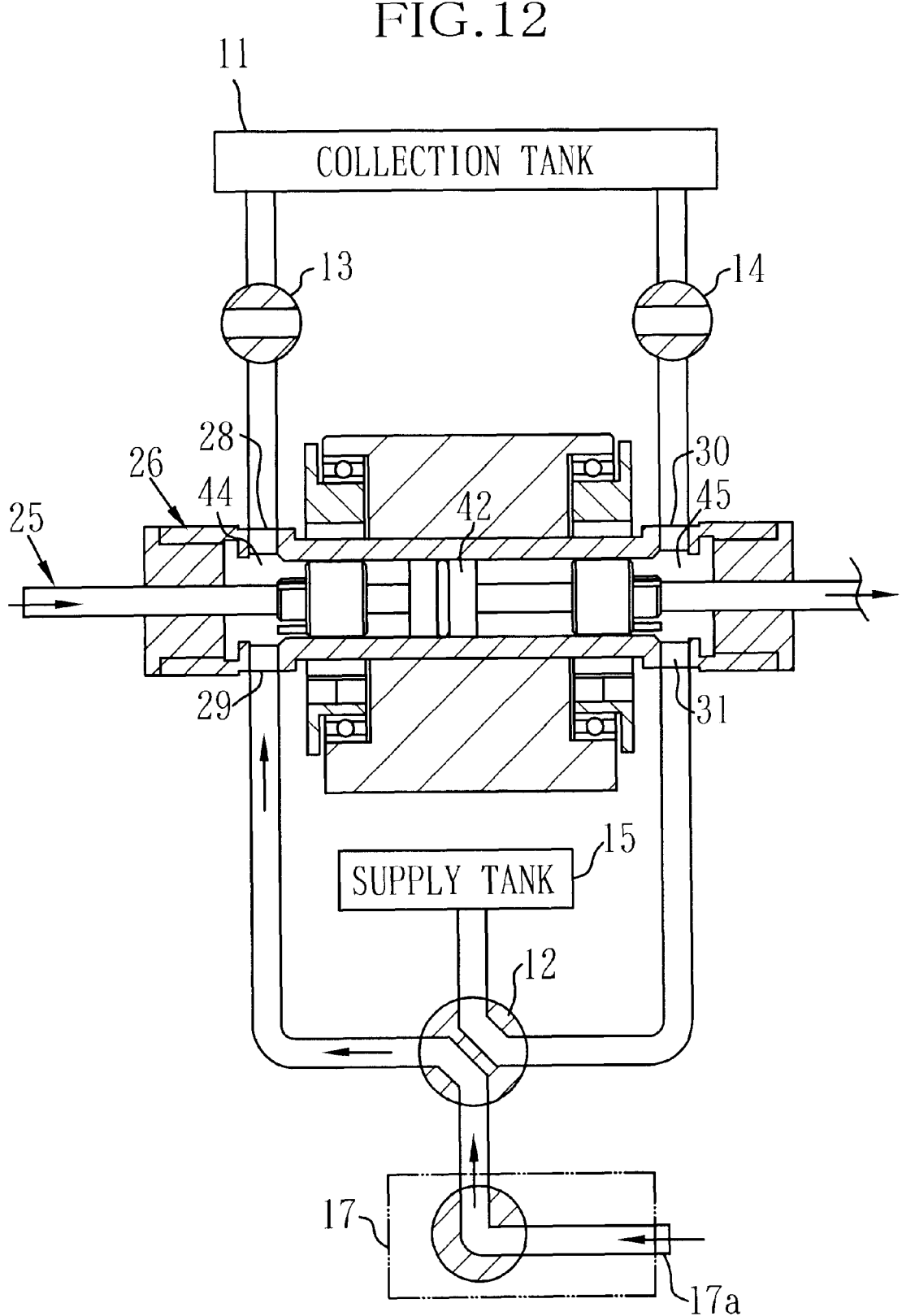
FIG. 12 is an explanatory diagram illustrating the lubricant coating system of FIG. 1 in a drip prevention step of the piston turning operation.

In the drip preventing step, the switching values 12 to 14 stay in the same positions as in the preceding dispensing operation, but the piston rod 25 and thus the piston 42 are moved slightly in the opposite direction to the preceding moving direction. Since the piston rod 25 is first moved forward in the dispensing operation in this instance, the switching valve 12 is set in the forth movement position, and the switching valves 13 and 14 are set in the closed position, as shown in FIG. 12, and the piston rod 25 is moved slightly backward. Thereby, the lubricant is sucked through the second port 29 back to the syringe 26, so the lubricant remaining in the nozzle 17a is prevented from dripping.

Figure 13:
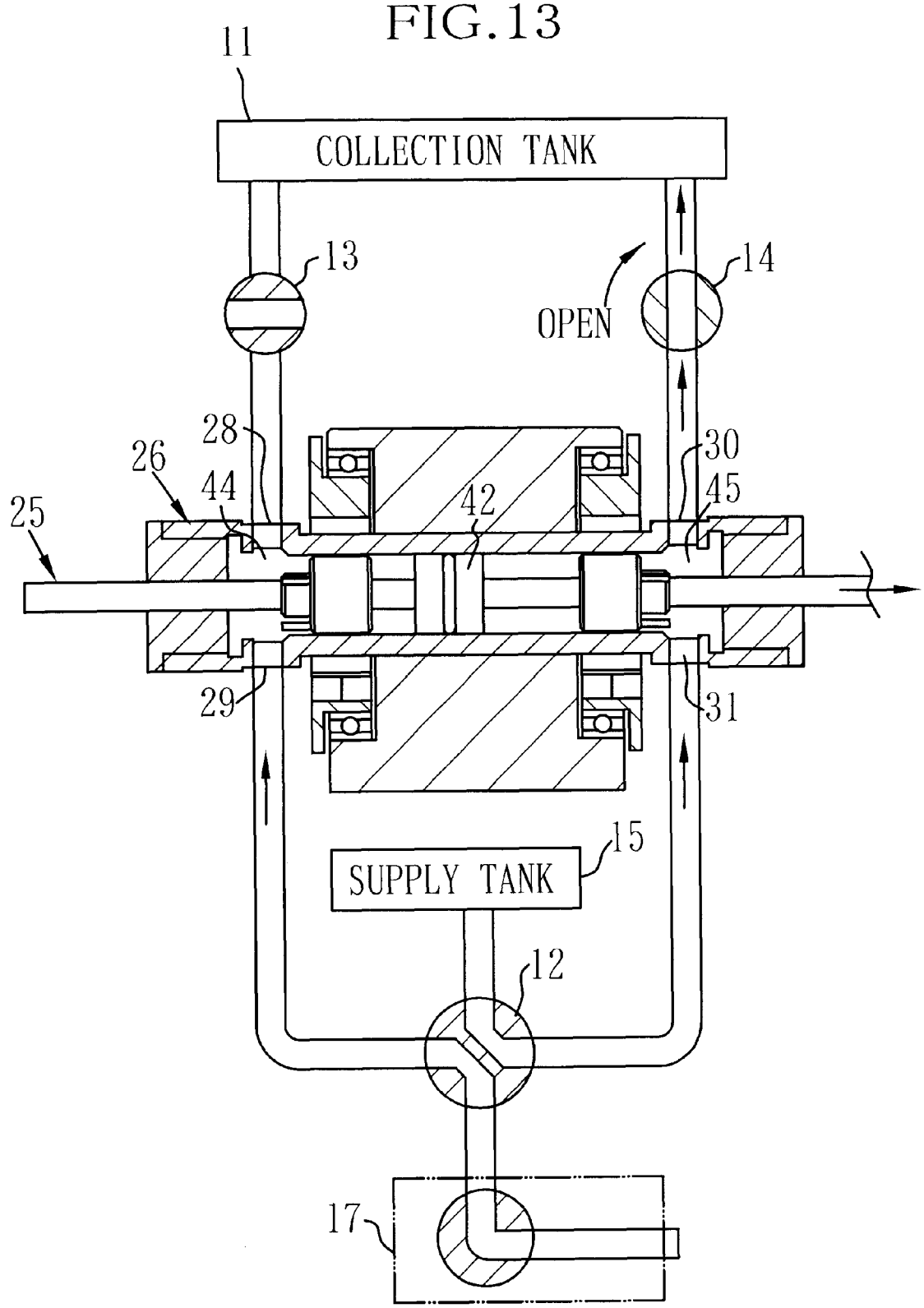
FIG. 13 is an explanatory diagram illustrating the lubricant coating system of FIG. 1 in a venting step of the piston turning operation.

The venting step follows the drip prevention step. In the venting step, the actuator 33 or 34 is driven to switch one of the two-way switching valves 13 and 14 that is on the sucking side in the preceding dispensing operation, i.e. the valve 14 in this instance, to the open position for a limited time, as shown in FIG. 13. While the valve 14 is turned open, the piston rod 25 is moved by a predetermined stroke in the opposite direction to the preceding movement, i.e. in the backward direction in this instance. Since the supply tank 15 is disposed above the collection tank 11, the lubricant flows from the supply tank 15 into the syringe 26 by itself, as the lubricant flows through the open valve 14 out of the syringe 26 into the collection tank 11, because of the difference in height between the supply tank 15 and the collection tank 11. Thereby, bubbles that have been produced in the lubricant because of negative pressure inside the syringe 26 flow with the lubricant into the collection tank 11, so the bubbles are eliminated from inside the syringe 26. The stroke of the piston rod 25 propels venting the bubbles contained in the lubricant out to the collection tank 11. The stroke of the piston rod 25 for the venting step is determined smaller than that for the dispensing operation, but may be equal to or larger than the stroke for the dispensing operation.

Since the first and third ports 28 and 30 are formed on the top sides of the large diameter sections 44 and 45, and the air entering the syringe 26 or the bubbles generated in the syringe 26 tend to come together in the top sides of the large diameter sections 44 and 45, the bubbles are efficiently exhausted. Venting or exhausting the bubbles prior to the dispensing operation prevents the bubbles from being increased by the dispensing operation, and thus facilitates making the dispensing operation in continuous succession. It is to be noted that the venting step may be executed only by opening one of the valves 13 and 14 that is in the sucking side in the preceding dispensing operation, without driving the piston rod 25.

After the venting step, either of the two-way switching valves 13 and 14 is reset to the closed position, and the four-directional switching actuator 35 is driven to switch the four-way switching valve 12 to the other position than before, i.e., to the back movement position in this instance, as shown in FIG. 3. Thereby, the second port 29 that has functioned as an ejection port in the preceding dispensing operation is changed to a sucking port.

Thereafter, the pre-stroking step is executed by driving the rod driving actuator 24 to move the piston rod 25 and thus the piston 42 in the backward direction by a small amount. Thereby, bubbles generated by the switching of the four-way switching valve 12 are let out of the syringe 26, and the lubricant is fed to the needle valve 17, driving out the air that has been sucked into the needle valve during the drip prevention step. Simultaneously, the control section 40 drives a shift mechanism 70 to insert an anti-sprinkle plate 71 into front of the nozzle 17a, so that the lubricant from the nozzle 17a may not be sprinkled. After the shift mechanism 70 retracts the anti-sprinkle plate 71 from the front of the nozzle 17a, the cleaning mechanism 22 is activated to clear the lubricant off the nozzle 17a. Thereafter, the piston rod 25 is moved by the constant stroke in the backward direction to dispense the lubricant. As described so far, since the piston rod 25 is moved in the same direction in the piston turning operation as in the following dispensing operation, the lubricant coating system 10 can start the dispensing operation immediately. When the piston rod 25 and thus the piston 42 reach a terminal in the backward direction, the piston turning operation is executed in the same way as set forth above, while moving the piston rod 25 in the same direction as in the following dispensing operation.

As long as the normal mode is continued, the above described operations are repeated to put the lubricant on the objects to coat 18 successively.

Although the stirring blades 53 and 54 protrude in parallel to the piston rod 25 in the present embodiment, it is possible to incline the stirring blades 53 and 54 to the axial direction of the piston rod 25, so as to cause the lubricant to whirl in the axial direction. The stirring blades may be oriented in a perpendicular direction to the axis of the piston rod 25. The number of stirring blades 53 and 54 and the number of magnets 55, 56, 59 and 60 are not limited to the above embodiment, but may be modified appropriately. The arrangement of the stirring blades as well as the magnets in the stirrer may be modified appropriately.

Now the operations in the standby mode will be described. In the standby mode, the control section 40 keeps on monitoring the sensors 71 and 72, so that the lubricant coating system 10 may return to the normal mode as soon as it is allowed.

Figure 14:
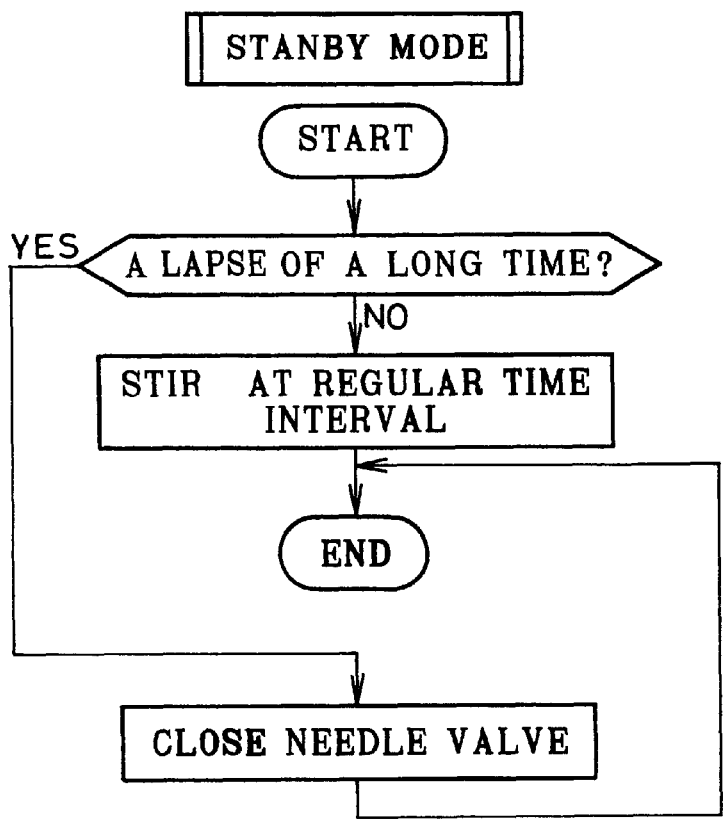
FIG. 14 is a flow chart illustrating a sequence of a standby mode of the lubricant coating system.

In the standby mode, as shown in FIG. 14, the stirring actuators 51 and 52 are driven to rotate both of the stirrers 47 and 48 for a time intermittently at regular intervals. One of the stirrers 47 and 48 that is on the sucking side of the syringe 26 at the start of the standby mode continues rotating during the standby mode as in the normal mode. Therefore, strictly speaking, the other stirrer 47 or 48 is driven to rotate intermittently during the standby mode. Thus, the density of the lubricant is maintained constant in the syringe 26.

When a predetermined long time has elapsed from the start of the standby mode, the piston rod 25 is moved in the opposite direction to the preceding moving direction for the sake of making the same drip preventing operation as described before with respect to the piston turning operation. Thereafter, the valve member 17a of the needle valve 17 is closed, for preventing the lubricant from evaporating.

Figure 15:
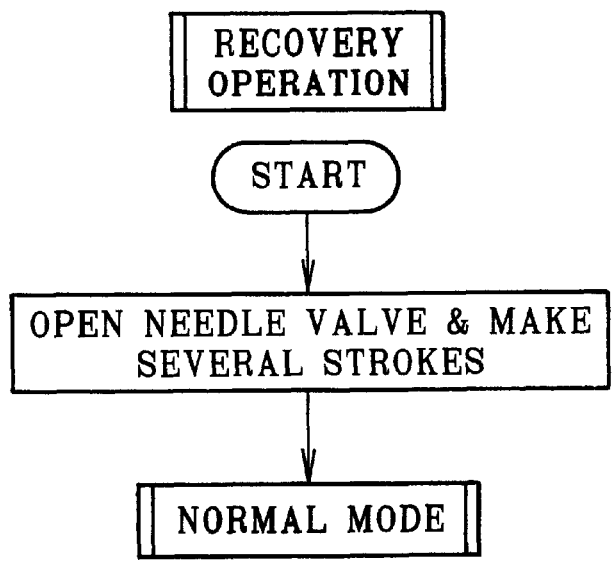
FIG. 15 is a flow chart illustrating a sequence of a recovery operation from the standby mode to the normal mode.

When the lubricant coating system 10 returns to the normal mode from the standby mode after the valve member 17a is closed, a recovery operation is executed. In the recovery operation, as shown in FIG. 15, the on-off valve 17b is opened, and the piston rod 25 is moved by several strokes, to supply the lubricant to the needle valve 17, thereby to drive the air out of the needle valve 17. The number of strokes for this operation is determined such that the lubricant is ejected from the nozzle 17a without fail. The shift mechanism 70 is activated during the recovery operation, to insert the anti-sprinkle plate 71 in front of the nozzle 17a. After the shift mechanism 70 retracts the anti-sprinkle plate 71 from the front of the nozzle 17a, the cleaning mechanism 22 is activated to clear the lubricant off the nozzle 17a. Thereafter, the piston rod 25 is moved by the constant stroke in the backward direction to dispense the lubricant.

Figure 16:
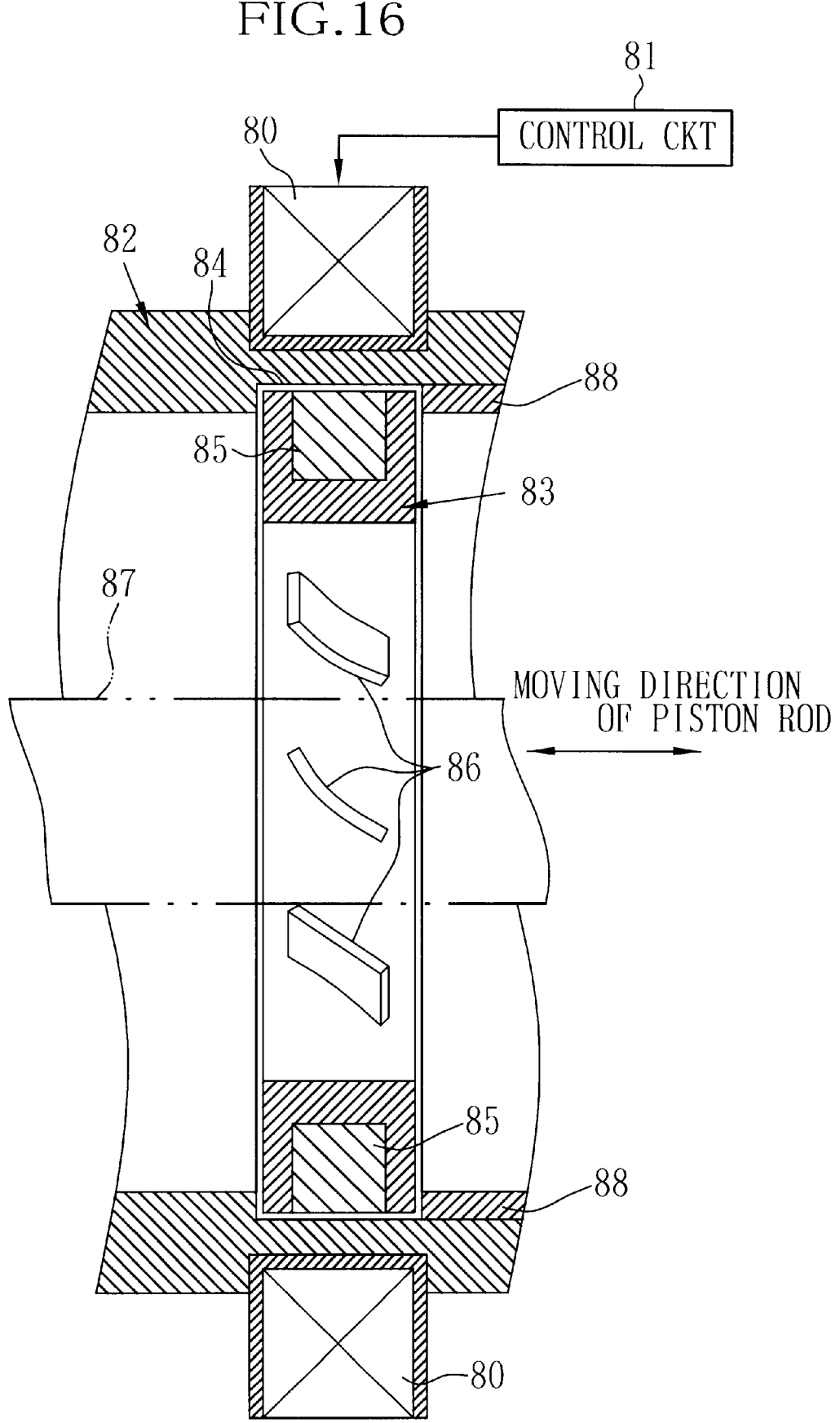
FIG. 16 is a fragmentary sectional view of a stirrer and a stirrer driving device according to another embodiment of the present invention.

In the above embodiment, the stirrers 47 and 48 are mounted rotatable on the piston rod 25. According to another embodiment, as shown in FIG. 16, a ring-like stirrer 83 is fitted in a groove 84 that is provided around an inner periphery of a syringe 82, such that the stirrer 83 may turn around a piston rod 87 while being guided along the groove 84. The groove 84 is formed by a recessed inner peripheral portion of the syringe 82 and a sleeve 88 that is fit in the syringe 82 from its one end. In this embodiment, a number of stirring blades 86 are provided at regular intervals on an inner periphery of the stirrer 83 and are protruded radially inward to an extent that the stirring blades 86 will not interfere with the piston rod 87. As shown in FIG. 16, it is preferable to incline the stirring blades 86 to the axial direction of the piston rod 87, so as to cause the fluid to whirl in the axial direction in the syringe 82.

Although the stirrer drive rings 49 and 50 that are rotated around the syringe 26 by the stirring actuators 51 and 52 are provided as a stirrer driving device for rotating the stirrers 47 and 48 in the above embodiment, a stirrer driving device of the present invention may be configured differently. For example, according to the second embodiment shown in FIG. 16, a magnetic coil 80 and a control circuit 81 constitute the stirrer driving device. The magnetic coil 80 is constituted of a plurality of coils that generate rotary magnetic fields at three or four regularly spaced positions around the syringe 82. The stirrer 83 has at least two magnets 85 in diametrically opposite circumferential positions thereof, the magnets 85 generating magnetic fields in the radial directions of the stirrer 83. The control circuit 81 generates electric current for exciting the magnetic coils 80 in those phases necessary for rotating the stirrer 83.

EXAMPLE

The syringe 26 is preferably formed from a non-magnetic material, such as resin, ceramic or glass. As the resin, transparent PFA (perfluoro-alkoxy fluoroplastics) is prefer-able. The stirrers 47 and 48 are preferably formed from a resin or a ceramic. The stirrer drive rings 49 and 50 are preferably formed from a non-magnetic material, such as resin or brass.

The lubricant coating system 10 of the above embodiment is preferably applicable to a recycling system of a lens-fitted photo film unit. In that case, a shutter mechanism of a used lens-fitted photo film unit is assumed to be the object to coat 18. The lens-fitted photo film unit is constituted of a main body that contains a photo filmstrip therein and has exposure mechanisms mounted thereon, and front and rear covers that cover the main body portion from the front and rear sides. The exposure mechanisms include a taking lens, the shutter mechanism, and a winding lock mechanism, and are expected to be reused. As well-known in the art, the shutter mechanism consists of a shutter drive lever, a shutter blade, a shutter charging spring, and a returning spring. The shutter blade usually closes a shutter opening that is located behind the taking lens, and may swing in a plane perpendicular to an optical axis of the taking lens. The shutter drive lever may rotate on an axis that extends in a vertical direction of the lens-fitted photo film unit, and kicks the shutter blade as it rotates from a charged position to a released position, causing the shutter blade to swing in a direction to open the shutter opening. The shutter charging spring is hooked at one end on a spring holding portion of the shutter drive lever, and at the other end on a portion other than the shutter drive lever, such that the shutter charge spring urges the shutter drive lever to the released position. The returning spring urges the shutter blade to return to the initial position closing the shutter opening.

The used lens-fitted photo film unit is collected and disassembled in a factory for recycling. In the recycling system, some parts are sorted to be recycled as materials, and other parts are reused as it is for assembling a new product. As for the lens-fitted photo film unit, since the main body is covered with the front and rear covers, the main body is little stained or damaged in most cases, so the main body is expected to be reused. Before reusing the main body, the exposure mechanisms are inspected to check if these mechanisms operate properly. According to the inspection, the speed of movement of the shutter blade tends to be changed depending upon under what conditions the collected lens-fitted photo film unit has been used. But it has been found that the variations in the shutter speed can be reduced to a predetermined tolerable range, without exchanging the parts, if only a lubricant is put on the engagement between the one end of the charging spring and the spring holding portion of the shutter drive lever. The lubricant coating system 10 of the present invention is effectively usable for this purpose. After being coated with the lubricant, the speed of the shutter blade is measured a number of times, to check if the speed variation is in the tolerable range.

As the lubricant, a liquid type lubricant that is composed of an oil component with a high fluidity at a low temperature, and an ultrafine fluoroplastic is suitable for the shutter mechanism. Exemplary of such liquid type lubricant is Dry Surf HF-1800 (trade name), produced by Herves Ltd. This lubricant is called a dry coating lubricant, looks opaque white, has no flash point in the open-cup flash point test, is usable in a range from −30° C. to 120° C., and has a specific gravity of 1.25 at 25° C. After the coating, the surface of this lubricant is half-wet. Also, this lubricant includes no factor of destroying the ozone, lasts for 4.1 years in the atmosphere, and the GWP is 500 ($CO^2$=1). Accordingly, this type of lubricant is highly volatile and contains solid components, so the density will change while it is stored in a hermetic container. To keep the density constant, the above described lubricant coating system 10 provided with the mixing devices is preferable. The amount of lubricant to put on the individual main body of the lens-fitted photo film unit is preferably 0.001 cc to 0.01 cc.

Since the piston rod 25 is moved back and forth in the lubricant coating system 10, the lubricant may be dispensed successively. Because the lubricant contains the solid components, the lubricant is being stirred in the sucking side of the syringe 26 even during the dispensing operation. Since the lubricant is highly volatile, the on-off valve 17b of the needle valve 17 is closed when the standby mode continues for a long time. However, the present invention is applicable not only to dispensing the above described lubricant, but any kind of fluid may be dispensed by the dispenser of the present invention.

Meanwhile, it is very important to clear optical members off of dusts, sands and stains, since these extraneous objects remarkably lower the optical performances. Because optical members of the lens-fitted photo film unit, such as a taking lens and a finder lens, are more likely to get stained or scratched, it is necessary to inspect the optical members each individually before reusing them.

For this purpose, these lenses have conventionally been inspected by naked-eyes on the basis of a limit sample, but this conventional method is inefficient and is inferior in reliability. To solve this problem, Japanese Laid-open Patent Application No. 8-304052 discloses a lens inspection device that scans the lens surface with a spot light beam across a constant direction, and photo-electrically detects light that is transmitted and scattered through the lens. Because the transmitted light is scattered if the lens has any defect, e.g. get scratched or stained, the lens inspection device generates a defect signal when the detected signal goes above a preset level. This inspection device makes it possible to detect strains or scratches on the lens through comparison of the signal level with the preset level, and thus accomplish efficient and quantitative evaluation.

Since the above conventional inspection device scans a spot light beam along a line, the inspection cannot be so speedy. Besides, where the lens has a scratch or a strain in the scanning direction, the transmitted light is little scattered so it is difficult to detect them accurately.

Moreover, because the stain on the lens surface reflects or deflects some fragment of the incident light, so the intensity of the transmitted light is decreased. Therefore, an optimum photo-sensitivity for detection of the stains is considered to be different from that for detection of the scratches. However, since the above conventional inspection device inspects any kinds of defects of the lens in the same way, the reliability is unsatisfactory.

FIGS. 17 to 29 show a lens inspection system that permits detecting scratches, extraneous objects, such as stains, and other kinds of defects of an optical member with high accuracy. That is, according to the following embodiment, a light beam is projected from one side onto a lens to inspect, and a light transmitted and scattered through the lens is photo-electrically detected as a dark field image of the lens on the other side of the lens, and when the intensity of the photoelectric signal detected from an inspection range of a photoelectric imaging device goes above a preset level, the lens is judged to be defective.

In the present embodiment, the light is projected onto the entire surface of the lens at once and a dark field image of the lens is photographed through a photoelectric element. Therefore, the inspection becomes speedy. Since the defection sensitivity would not fluctuate depending upon the direction of existence of the defects, any kinds of defects are detected without fail.

Figure 17:
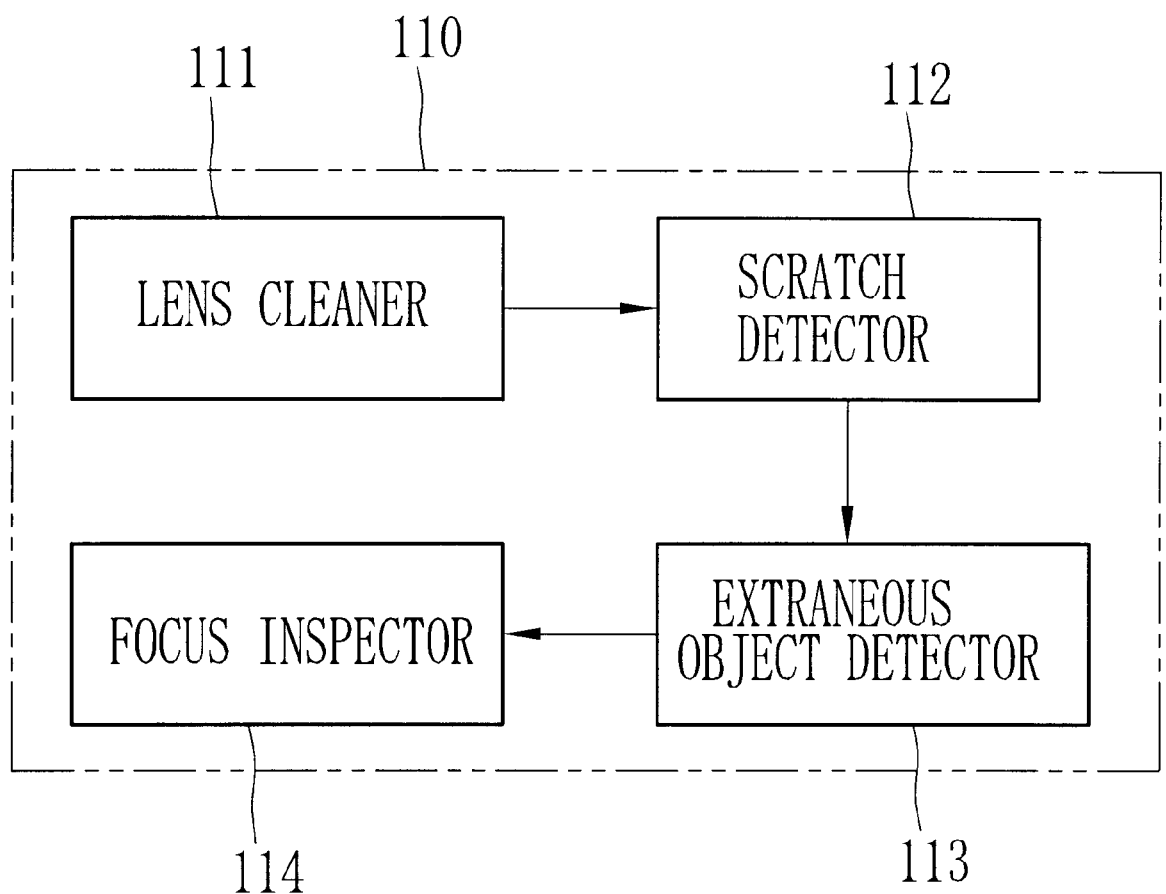
FIG. 17 is a block diagram illustrating a taking lens inspection system according to another embodiment of the present invention.

The lens inspection system according to the present embodiment is adapted to inspecting the taking lenses of the lens-fitted photo film units. As shown in FIG. 17, the lens inspection system for the lens-fitted photo film unit, hereinafter referred to as the inspection device 110, is mainly constituted of a lens cleaner 111, a scratch detector 112, an extraneous object detector 113 and a focus examiner 117.

Figure 18:
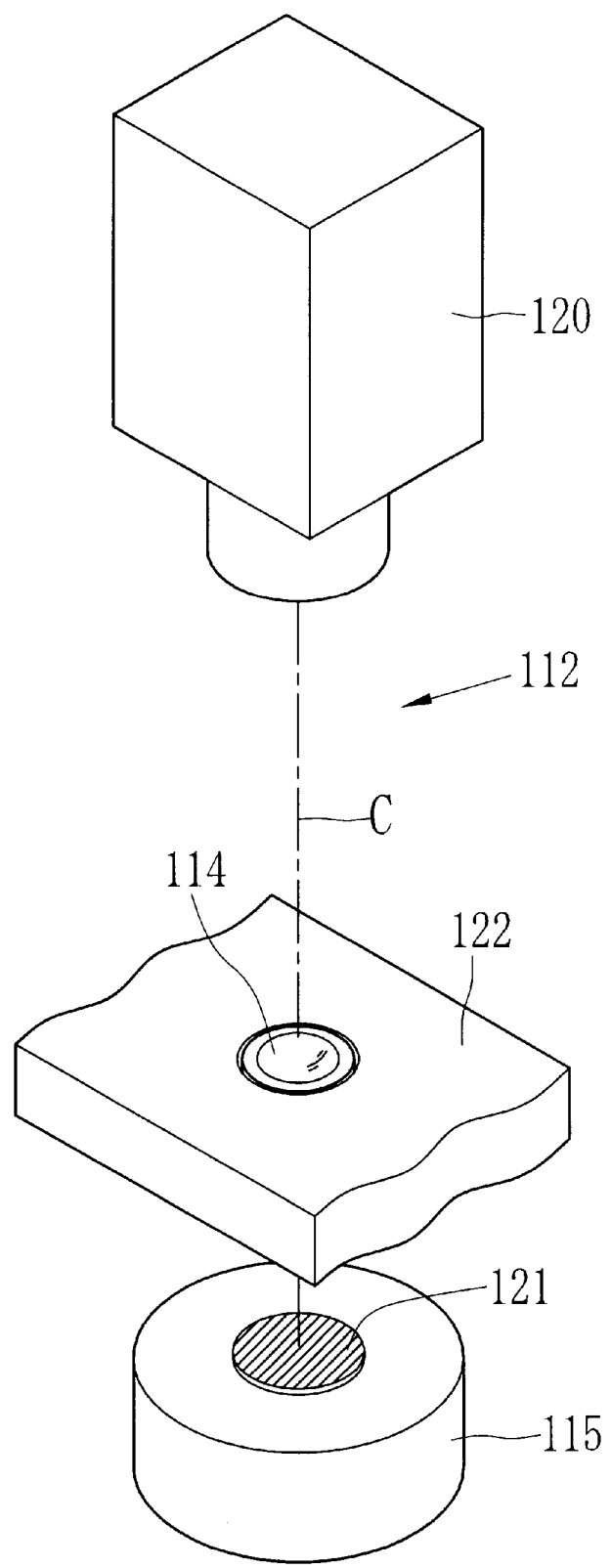
FIG. 18 is a perspective view of a scratch detector of the taking lens inspection system of FIG. 17.
Figure 19:
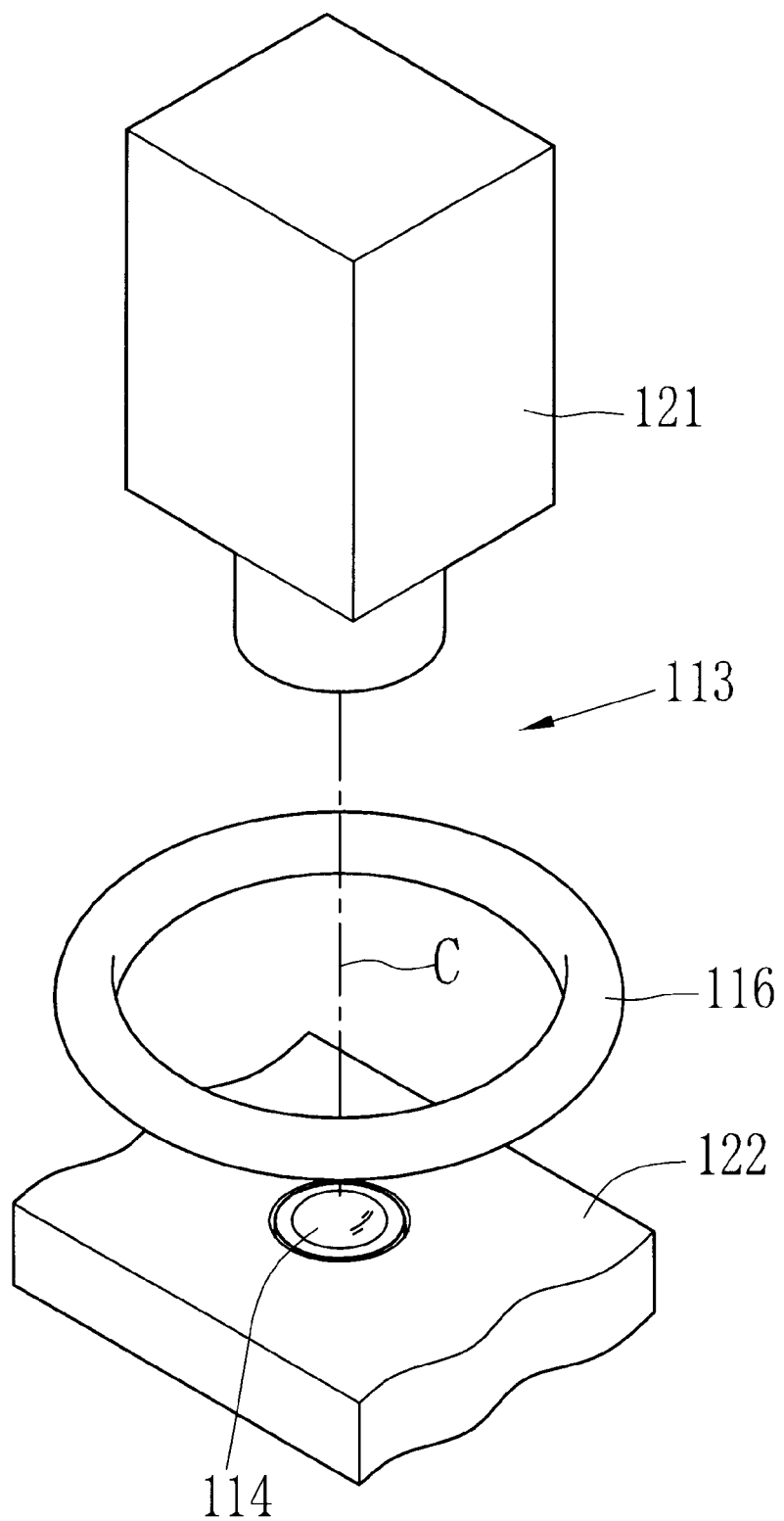
FIG. 19 is a perspective view of an extraneous object detector of the taking lens inspection system of FIG. 18.

As shown in FIGS. 18 and 19, the scratch detector 112 and the extraneous object detector 113 are each provided with a light projector 115 or 116 for projecting inspection light onto a taking lens 114, and an imaging device 120 or 121 that picks up electric signals from an optical image of a convex surface 114a of the taking lens 114, respectively. The taking lens 114 to inspect is held in a recess that is formed in a top surface of a specific pallet 122. The pallet 122 is successively conveyed by a not-shown pallet conveyer mechanism from the scratch detector 112 to the extraneous object detector 113.

Figure 20:
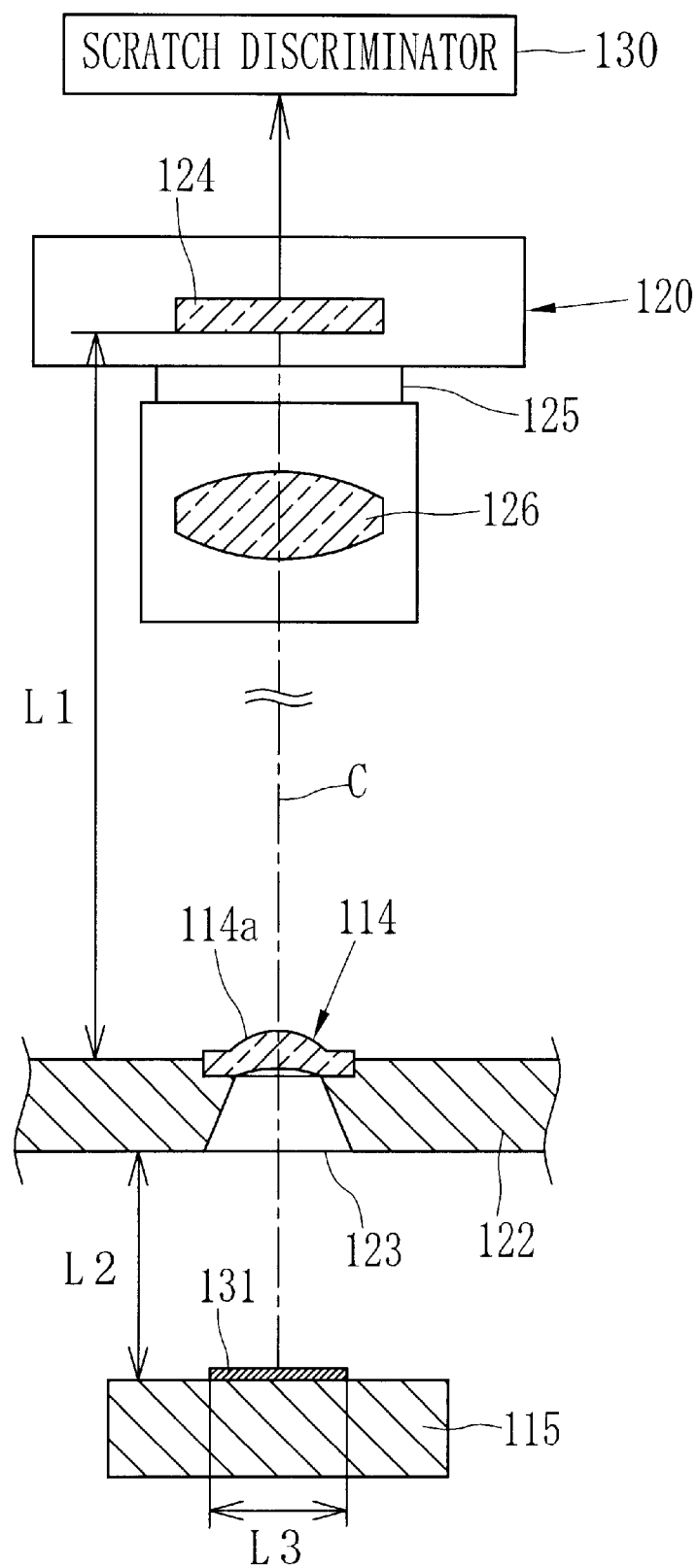
FIG. 20 is a schematic diagram illustrating the scratch detector of FIG. 18.

Referring to FIG. 20 showing the scratch detector 112, the pallet 122 holding the taking lens 114 is positioned in between the light projector 115 and the imaging device 120, with the convex surface 114a of the taking lens 114 oriented upward. A substantially cylindrical aperture 123 is formed from the bottom of the recess through the bottom surface of the pallet 122, so the inspection light from the light projector 115 is projected from the bottom side onto the taking lens 114. To prevent eclipse of the inspection light from the light projector 115, the aperture 123 has a smaller diameter on the side of the taking lens 114. In this instance, on condition that the pallet 122 has a thickness of 8 mm, the aperture 123 has a diameter of 7.5 mm in on the side of the taking lens 114, and a diameter of 13 mm on the side of the light projector 115.

The imaging device 120 is constituted of a CCD image sensor 124 having photo sensor cells, called pixels, arranged in a two-dimensional matrix, a close-up ring 125 and an image forming lens 126 that are attached to the front of the CCD image sensor 124. The taking lens 114 is positioned such that an optical axis C of the taking lens 114 coincides with an optical axis of the image forming lens 126 and centers of the close-up ring 125 and the CCD image sensor 124. An optical image of the taking lens 114 is formed through the image forming lens 126 on a photoelectric conversion surface of the CCD image sensor 124, so photoelectric signals whose intensities are proportional to the intensities of the incident light on the individual pixels are sent from the imaging device 120 to a scratch discriminator 130.

It is to be noted that the focal length of the image forming lens 126 may be set in a range from 16 mm to 50 mm, and that the close-up ring 125 is adjustable in a range from 6 mm to 40 mm. Also, a spacing L1 between the top surface of the pallet 122 and the CCD image sensor 124 may be set in a range from 30 mm to 200 mm. In this instance, the focal length of the image forming lens 126 is set at 50 mm, and the close-up ring 125 is set at 30 mm, whereas the spacing L1 is set at 130 mm.

Figure 21:
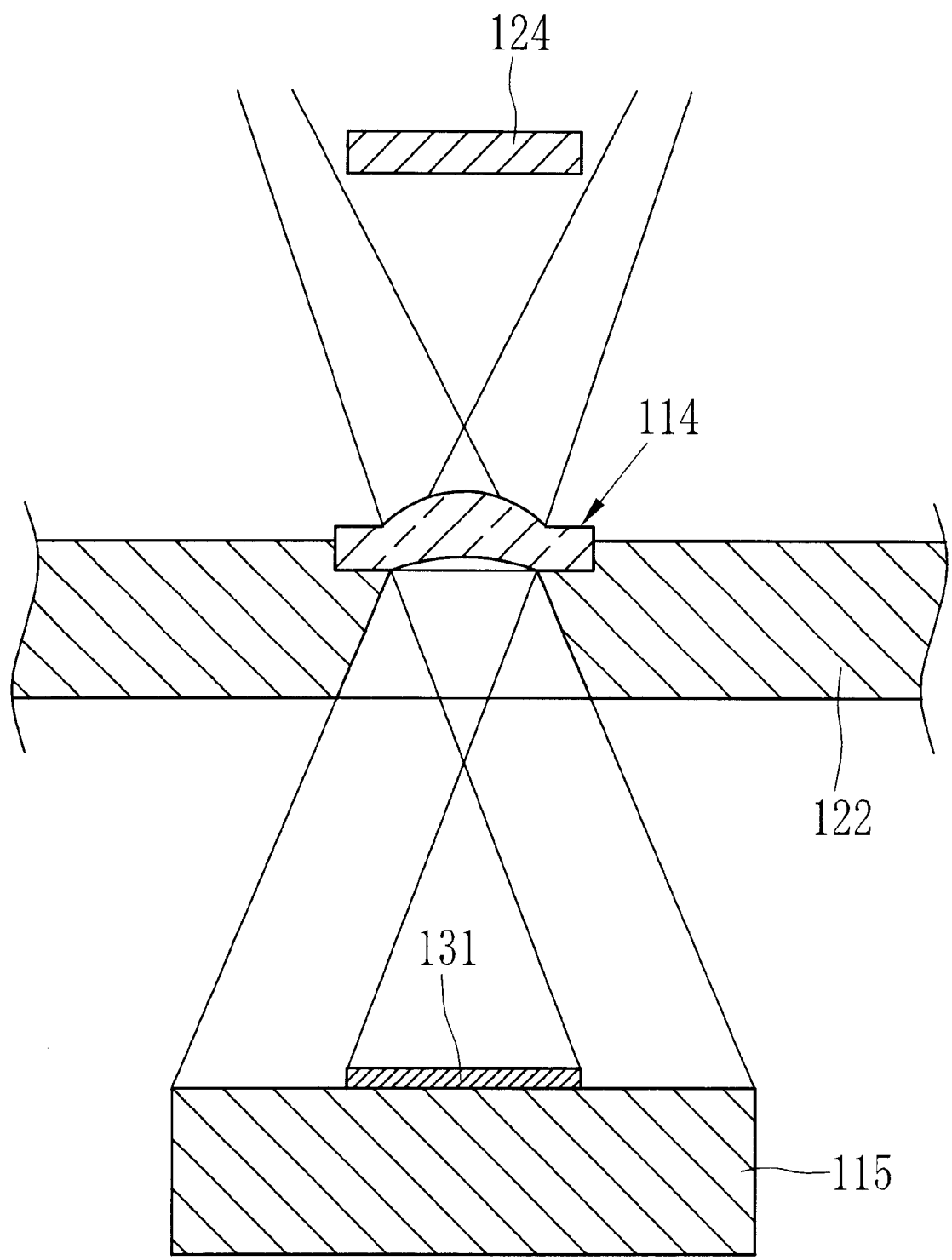
FIG. 21 is an explanatory diagram illustrating optical paths of inspection light projected onto a lens having no scratch in the scratch detector of FIG. 18.

The close-up ring 125 is fixed in a distance L2 from the bottom surface of the pallet 122. A not-shown red LEDs are built in the close-up ring 125 to project the inspection light uniformly onto the taking lens 114. A blinding mask 131 is mounted on a center of the light projector 115 so as to prevent inclusion of the light projector 115 in the photographic field of the imaging device 120. That is, as shown in FIG. 5, direct rays of the inspection light which are projected in the axial direction from the light projector 115 are prevented from falling on the photoreceptive surface of the CCD image sensor 124. Only indirect rays which are scattered through the taking lens 114 may fall on the photoreceptive surface. Accordingly, a dark field image of the taking lens 114 is formed on the CCD image sensor 124. Therefore, where the taking lens 114 has no scratch, as shown in FIG. 21, the intensities of the photoelectric signals are lower than a predetermined level.

Figure 22:
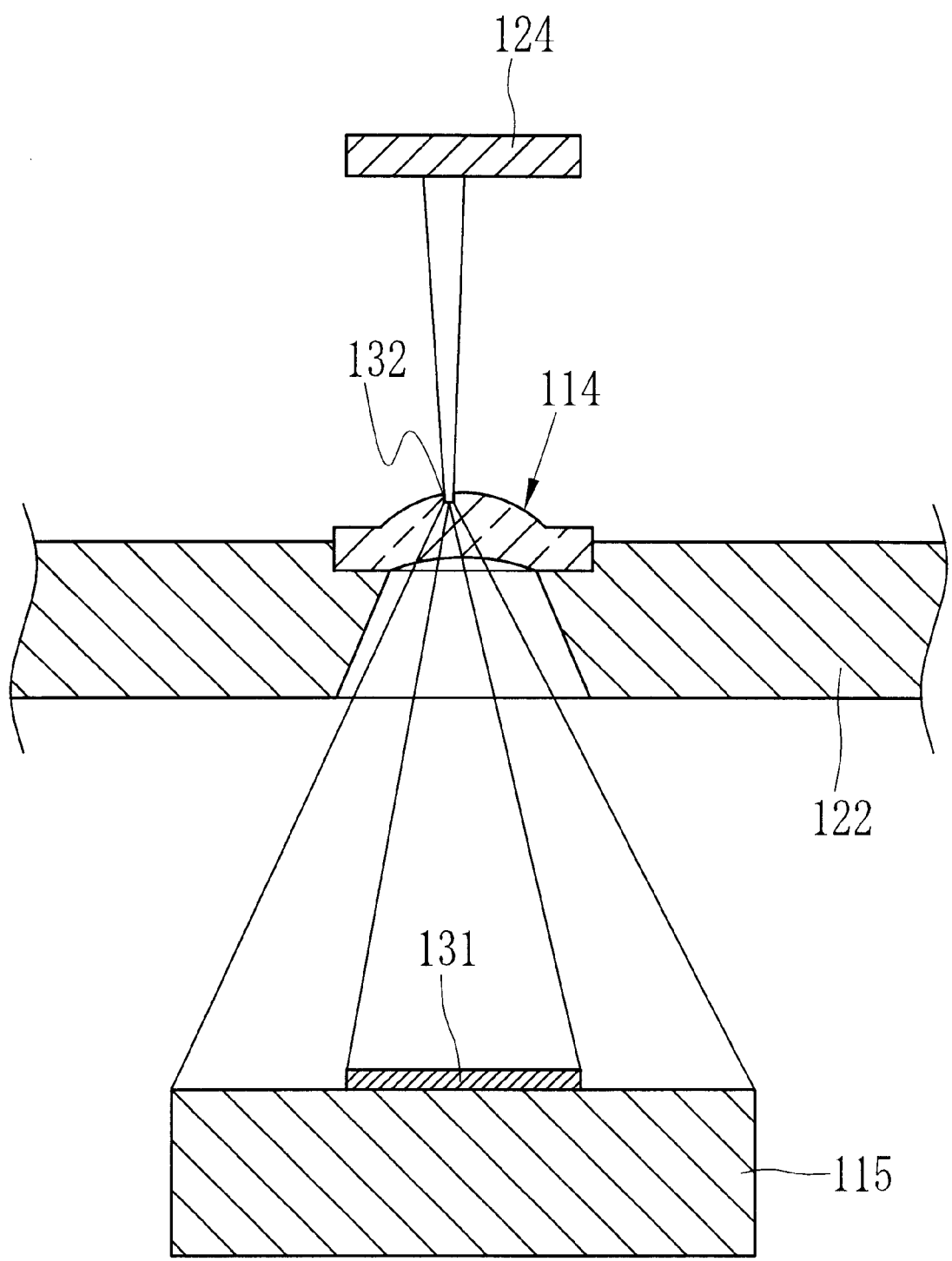
FIG. 22 is an explanatory diagram illustrating optical paths of inspection light projected onto a lens having a scratch in the scratch detector of FIG. 18.
Figure 23:
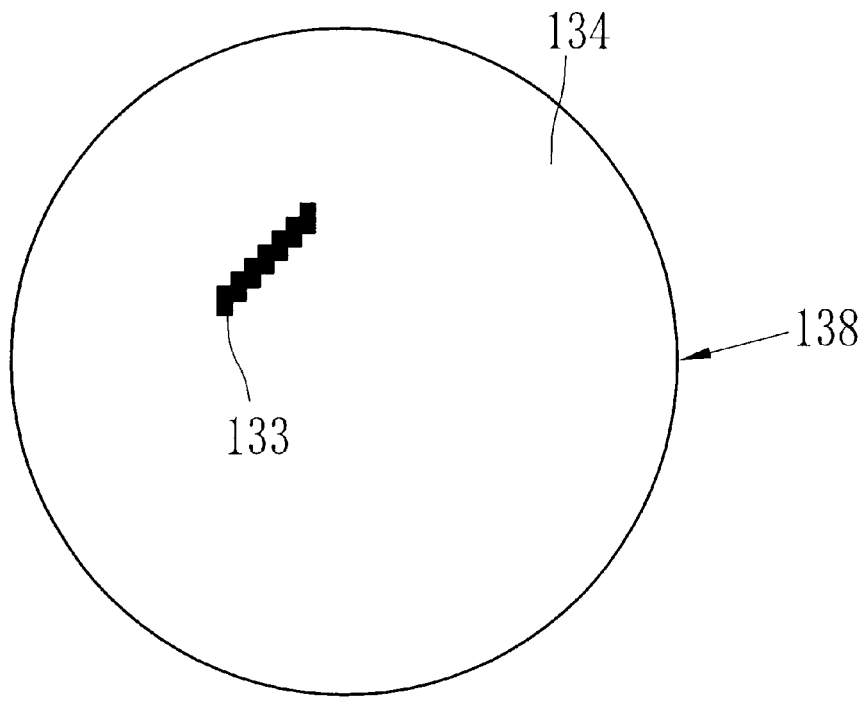
FIG. 23 is an explanatory diagram illustrating a light area in a dark field image of the lens.

On the contrary, if there is a scratch 132 on the taking lens 114, as shown in FIG. 22, some rays of the inspection light are scattered at the scratch 132, and is projected onto the CCD image sensor 124. In that case, the intensities of the photoelectric signals from those pixels of the CCD image sensor 124, onto which the scattered light rays fall are raised. Based on the photoelectric signals from the CCD image sensor 124, the scratch discriminator 130 determines whether the taking lens 114 gets any scratches or not. As shown for example in FIG. 23, the scratch 132 is detected by the scratch discriminator 130 as a light area 133 having a corresponding size to the scratch 132. For the sake of showing the light area 133 conspicuously, it is drawn in black in FIG. 23, whereas other dark area 34 is drawn in white. The blinding mask 131 may have a diameter L3 in a range from 10 mm to 20 mm insofar as it prevent the direct projection of the inspection light onto the CCD image sensor 124. In this instance, the diameter L3 is 12 mm.

In the scratch discriminator 130, a round range on the photoreceptive surface of the CCD image sensor 124, that is formed with a diameter of 6 mm about the optical axis C of the taking lens 114, is defined to be an inspection range 138, and the signal intensities from those pixels which are included in the inspection range 138 are represented by 8-bit tonal levels (0 to 255). The scratch discriminator 130 defines those pixels whose signal intensities are not less than "140" in the tonal level as light pixels, and checks if there is at least a light area consisting of the light pixels of a predetermined number, e.g. 110 or more, in the inspection range. If there is, the scratch discriminator 130 judges that the taking lens 114 gets scratched. If not, the scratch discriminator 130 judges that there is no scratch on the taking lens 114.

In the present embodiment, the threshold tonal level for the light pixel is set at "140", and the threshold pixel number for the light area is set at "110". But these threshold values may be modified appropriately according to the required inspection accuracy. Even if an individual scratch is so fine that it cannot be detected on the basis of the threshold values of the above embodiment, if there are a number of scratches, the optical performance is lowered below a reusable level. Therefore, in order to improve the inspection accuracy, it is preferable to set up the scratch discriminator 130 such that 130 judges the taking lens 114 to be defective when there are more than a predetermined number of fine scratches on the taking lens 114, as well as when there is a large scratch on the taking lens 114.

Figure 24:
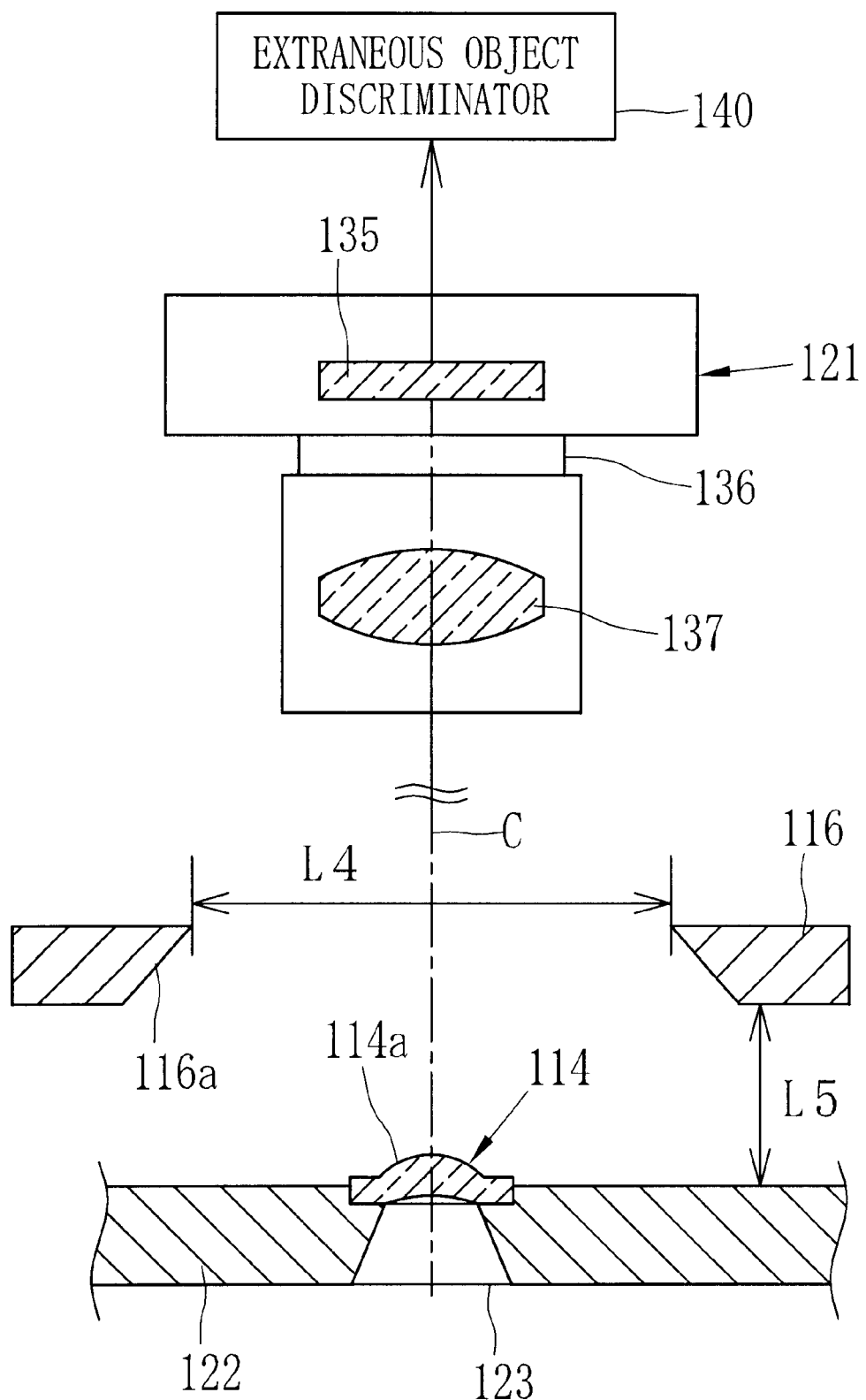
FIG. 24 is an explanatory sectional diagram illustrating the extraneous object detector of FIG. 19.

As shown in FIGS. 19 and 24, the imaging device 121 of the extraneous object detector 113 is constituted of a CCD image sensor 135, a close-up ring 136 and an image forming lens 137 in the same way as for the imaging device 120 of the scratch detector 112. The light projector 116 of the extraneous object detector 113 is substantially circular, and is disposed above the taking lens 114 with its center on the optical axis C of the taking lens 114, when the pallet 122 holding the taking lens 114 is positioned in the extraneous object detector 113. That is, the light projector 116 is disposed between the pallet 122 and the imaging device 121. Not shown LEDs are built in the light projector 116, and inspection light is projected from a projection surface 116a that is formed around an inner periphery of the light projector 116 and is oriented toward the taking lens 114 when it is positioned in the extraneous object detector 113. Thus, the inspection light from the light projector 116 is not directly projected onto the close-up ring 125, but only indirect rays scattered at the taking lens 114 can fall on the close-up ring 125. So the close-up ring 125 also takes a dark field image of the taking lens 114.

Figure 25:
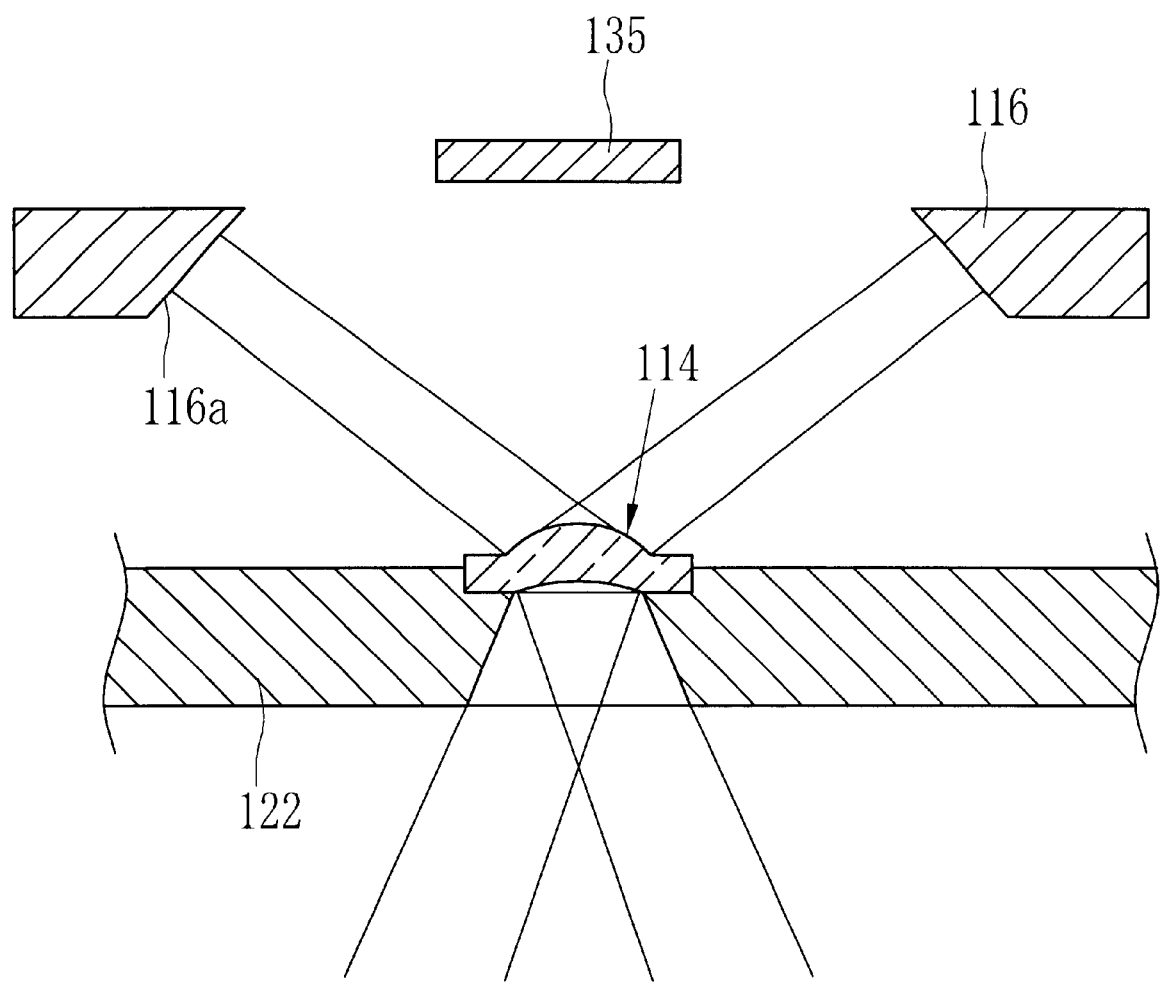
FIG. 25 is an explanatory diagram illustrating optical paths of inspection light projected onto a lens having no scratch in the extraneous object detector of FIG. 19.
Figure 26:
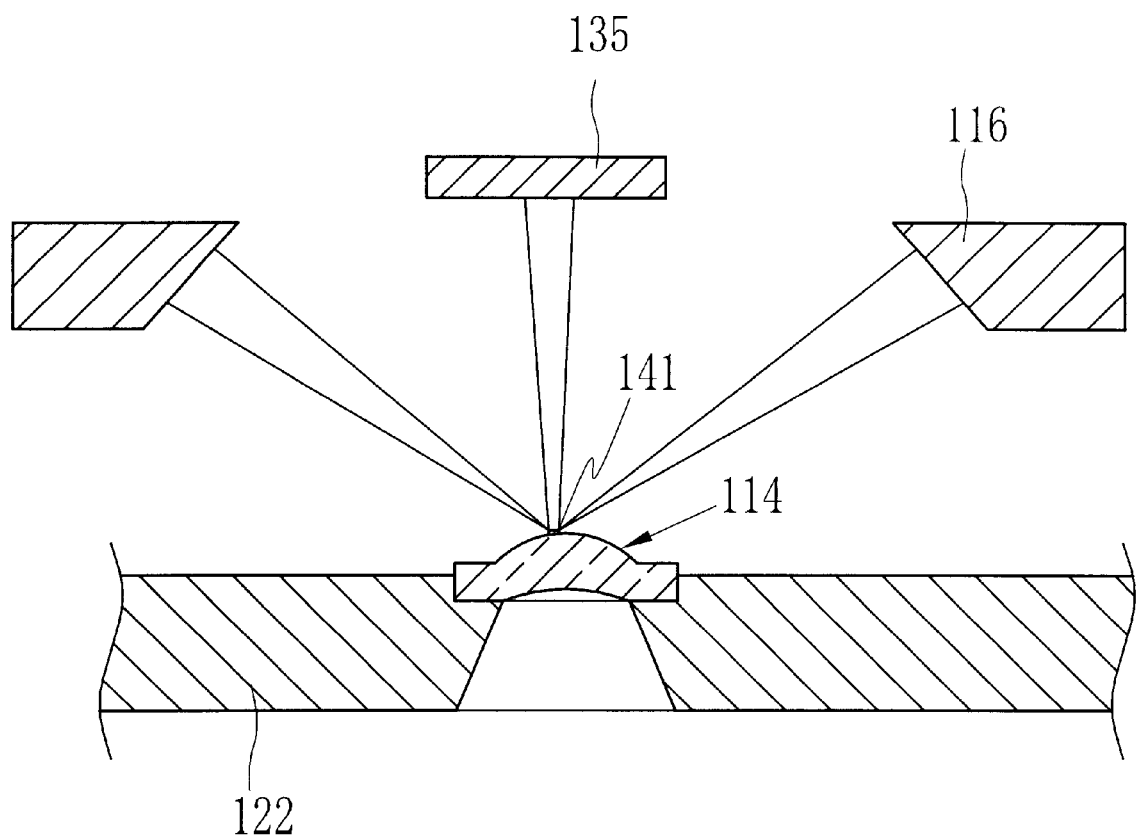
FIG. 26 is an explanatory diagram illustrating optical paths of inspection light projected onto a lens having a scratch in the extraneous object detector of FIG. 19.

If there is not an extraneous object on the taking lens 114, the inspection light passes through the taking lens 114, as shown in FIG. 25, so the intensities of photoelectric signals from respective pixels of the CCD image sensor 135 are low. On the contrary, if an extraneous object 141 is on the taking lens 114, as shown in FIG. 26, some rays of the inspection light from the light projector 116 are scattered at the taking lens 114 and fall on the photoreceptive surface of the CCD image sensor 135. As a result, the intensities of the photoelectric signals from those pixels corresponding to the position of the extraneous object 141 on the taking lens 114 are increased. The photoelectric signals are sent from the imaging device 121 to an extraneous object discriminator 140, so the extraneous object discriminator 140 determines based on the photoelectric signals whether there is any extraneous object on the taking lens 114 or not.

It is to be noted that the light projector 116 must have a large enough internal diameter L4 for preventing inclusion of the light projector 116 in a photographic field of the imaging device 121. However, too large internal diameter L4 lowers the illuminance on the taking lens 114 so much that the inspection accuracy is lowered. For this reason, the internal diameter L4 is preferably set in a range from 130 mm to 180 mm. In this instance, the value L4 is set at 130 mm. For the same reason, a spacing L5 between the top surface of the pallet 122 and the light projector 116 is preferably set in a range from 10 mm to 30 mm. In this instance, the value L5 is set at 16 mm.

Figure 27:
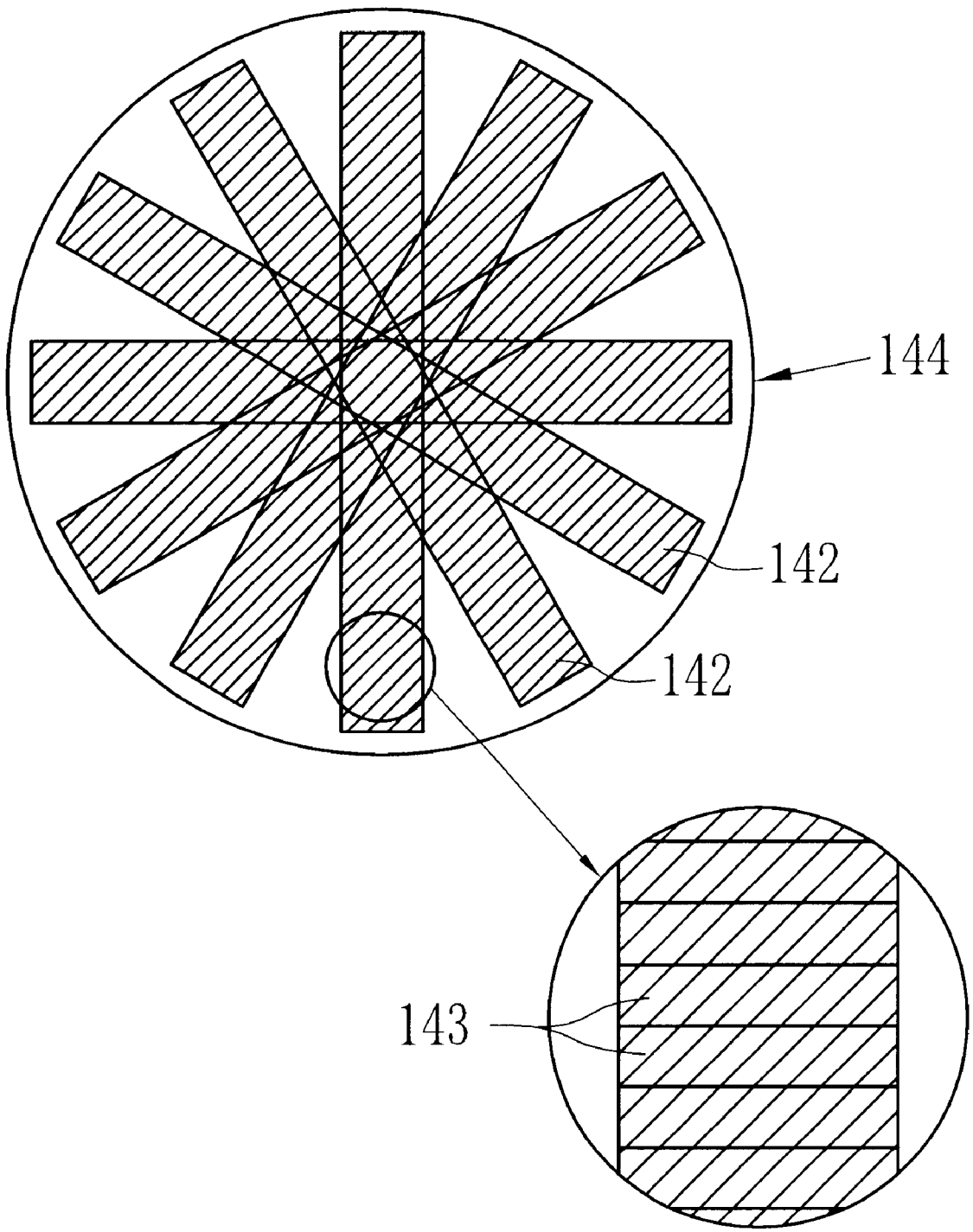
FIG. 27 is an explanatory diagram illustrating unit sections of an inspection range of an imaging device of the extraneous object detector of FIG. 19.

In the extraneous object discriminator 140, as shown in FIG. 27, a plurality of zones 142 having a width of 0.5 mm and extending in different diametrical directions are defined in an inspection range 144 that corresponds to the lens surface and thus the dark field image of the lens surface, and each zone 142 are sectioned into a number of rectangular segments 143 aligned in the diametrical direction. Each segment 143 has a length of 0.1 mm in the diametrical direction. The signal intensities from the pixels of the CCD image sensor 135 are also converted into 8-bit data representative of "0" to "255" tonal levels in the extraneous object discriminator 140. The extraneous object discriminator 140 calculates a mean value of tonal levels (an average tonal level) of those pixels which belong to the same segment 143. Thus, each segment 143 severs as an unit section of the inspection range 144. If a difference between the average tonal levels of adjacent two of the segments 143 is above "120", the extraneous object discriminator 140 judges that some extraneous object is put on the taking lens 114. When the difference in the average tonal level between the adjacent segments 143 is less than "120" with respect to every segment, the extraneous object discriminator 140 judges that there is no extraneous object on the taking lens 114.

Although the threshold value of the difference between the average tonal levels of the adjacent segments 143 for judgement in the extraneous object discriminator 140 is set at "120" in the present embodiment, the threshold value may be modified appropriately according to the required inspection accuracy. The size of the segments 143 may also be modified appropriately according to the fineness of the extraneous objects to detect.

Figure 28:
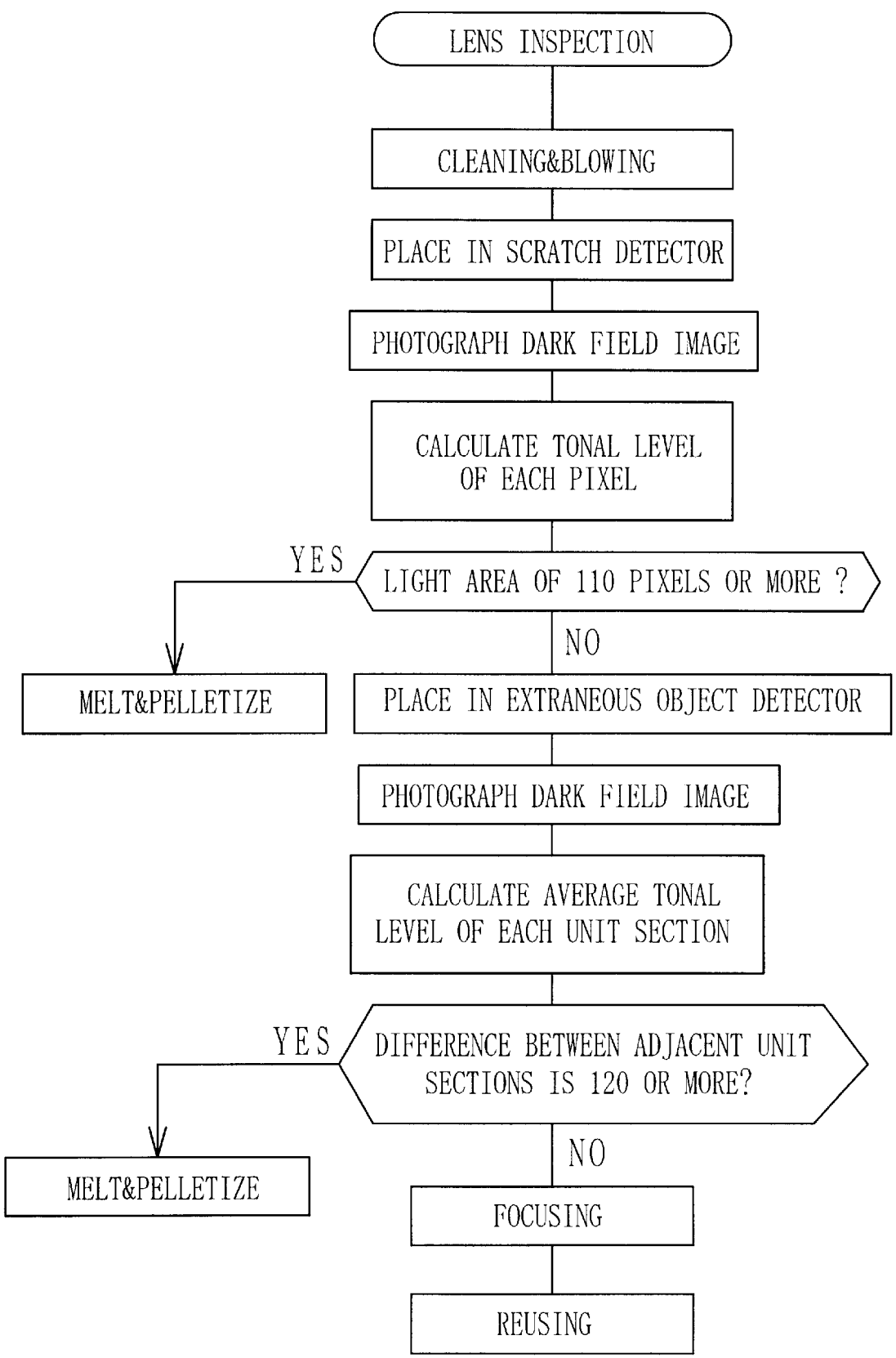
FIG. 28 is a flow chart illustrating an overall sequence of a taking lens inspection process included in a process of recycling taking lenses of lens-fitted photo film unit.

Next, the operation of the lens inspection device 110 will be described with reference to the flow chart of FIG. 28. Unit bodies of used lens-fitted photo film units are disassembled and sorted into respective components in an inspection factory. The taking lens 114 is separated from the unit main body, and is subjected to a cleaning and blowing process, for removing dusts and fats off of the surface of the taking lens 114.

After the cleaning and blowing process, the taking lens 114 is placed on the pallet 122, to be conveyed to the scratch detector 112. In the scratch detector 112, the light projector 115 projects the inspection light from the bottom side of the pallet 122 onto the entire surface of the taking lens 114 but diagonally to the optical axis C of the taking lens 114, so the imaging device 120 disposed above the taking lens 114 takes a dark field image of the taking lens 114. If there is any scratch on the taking lens 114, the inspection light is scattered at the scratch, so some rays fall on the CCD image sensor 124. The photoelectric signals obtained by the CCD image sensor 124 are sent to the scratch discriminator 130. The scratch discriminator 130 discriminates the light pixels whose tonal levels are not less than "140", and judges that the taking lens 114 has a scratch when there is an area consisting of not less than 110 successive light pixels. The taking lens 114 having any scratch may not be reused, so it is melted and pelletized. If the taking lens 114 is judged to have no scratch, it is conveyed to the extraneous object detector 113.

In the extraneous object detector 113, the circular light projector 116 projects the inspection light from above and around the convex surface 114a of the taking lens 114, and the imaging device 121 takes a dark field image of the taking lens 114. If there is any extraneous object on the taking lens 114, the inspection light is reflected from the extraneous object and falls on the CCD image sensor 135. The photoelectric signals obtained by the CCD image sensor 135 are sent to the extraneous object discriminator 140. The extraneous object discriminator 140 detects differences in average tonal level between every couple of adjacent segments 143, and judges that there is an extraneous object on the taking lens 114 when any of the differences is above 120.

The taking lens 114 that is judged to have any extraneous object is melted to be pelletized, or sent back to the cleaning and blowing process, and is inspected again. The taking lens 114 that is judged to have no extraneous object is conveyed to the focus inspector 117. After passing the inspection by the focus inspector 117, the taking lens 114 is allowed to be reused.

Figure 29:
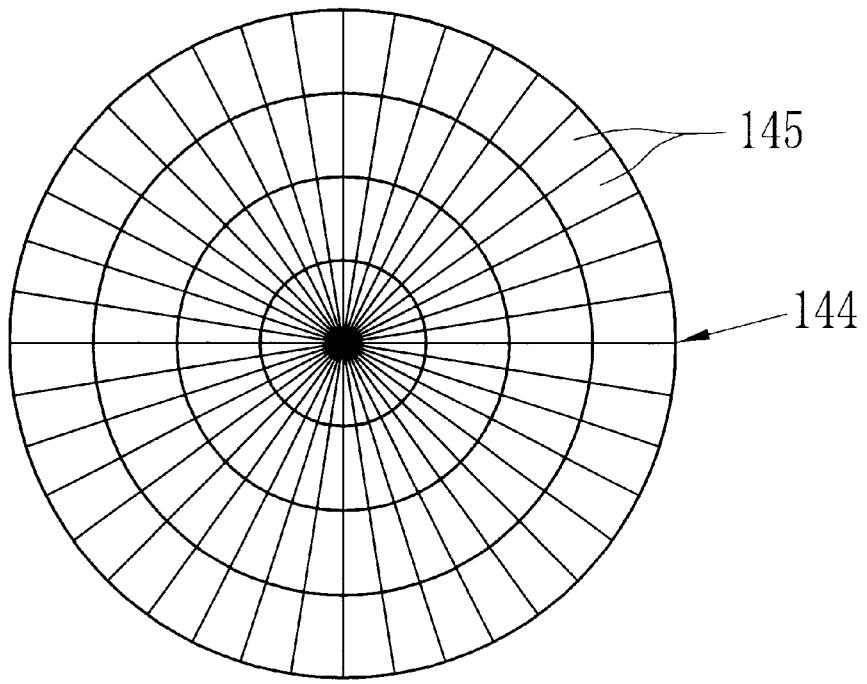
FIG. 29 is an explanatory diagram illustrating another pattern of unit sections of the inspection range of the imaging device of the extraneous object detector.

In the above embodiment, the extraneous object discriminator 140 defines the segments 143 in the diametrically extending zones 142 of the inspection range 144, as shown in FIG. 27. It is alternatively possible to section the inspection range 144 into concentrically and radially into sectors 145, as shown in FIG. 29, and calculate average tonal levels of the respective sectors 145. That is, each sector 145 constitutes an unit section of the inspection range 144 in this embodiment. The light source of the light projector 115 or 116 is not limited to the LEDs, but may be another kind of light source, such as a halogen lamp, insofar as it is able to project light uniformly onto the optical member to inspect.

Projecting the inspection light simultaneously onto the entire objective or image side surface of the lens achieves a quick inspection on the lens defects as compared to the conventional method where the inspection light is scanned linearly across the lens. Also the inspection accuracy becomes independent of the direction the defect exits.

Doing inspection for scratches separately from inspection for extraneous objects permits setting up an optimum inspection sensitivity for each kind of inspection. Since the inspection light is projected onto the lens from either side, if a defect cannot be detected when the inspection light is projected from the bottom side, the defect may be detected when the inspection light is projected from the top side. Especially because extraneous objects or stains are more likely to put on the objective side of the lens, inspection accuracy is remarkably improved by projecting the inspection light onto the objective side to detect extraneous objects or stains based on the reflected light from the objective side.

However, it is possible to execute either the inspection for scratches or the inspection for extraneous objects alone. Although the inspection for scratches is executed before the inspection for extraneous objects in the above embodiment, the sequence may be reversed. Covering the periphery of the scratch detector 112 and the extraneous object detector 113 with black light-shielding curtains protects the CCD image sensors 124 and 135 from ambient light, and thus contributes to increasing the inspection accuracy.

The present invention has been described with respect to the taking lens inspection device that inspects single-element convex lenses, the present invention is applicable also for inspection on concave lenses or on lens systems composed of a plurality of lens elements, if only the optics are arranged to make it possible taking the dark field image.

Thus, the present invention is not to be limited to the above embodiments but, on the contrary, various modifications are possible to those skilled in the art without departing from the scope of claims appended hereto.

What is claimed is:

1. A fluid dispenser having a syringe with ports on opposite ends thereof, a piston movable inside said syringe back and forth, and a supply tank being connectable alternately to one of said ports depending upon moving direction of said piston, said fluid dispenser dispensing a fluid from one of said ports that is located on the end of said syringe toward which said piston is moving, while sucking the fluid from said supply tank into said syringe through the other of said ports, said fluid dispenser comprising:

a pair of stirrers provided in said syringe on opposite sides of said piston, said stirrers being rotatable on a rotary axis that extends parallel to the moving direction of said piston; and a pair of stirrer driving devices disposed on an outer periphery of said syringe in correspondence with said stirrers, for driving said stirrers to rotate each individually by a magnetic force.

2. A fluid dispenser as recited in claim 1, wherein each of said stirrers has a plurality of magnets embedded therein symmetrically about said rotary axis of said stirrers, whereas said stirrer driving devices generate magnetic fields that cause said stirrers to rotate.

3. A fluid dispenser as recited in claim 1, wherein at least one of said stirrers is continuously rotated in one side of said piston, into which the liquid is being sucked.

4. A fluid dispenser as recited in claim 1, further comprising:

a piston rod that moves together with said piston and extends on the opposite sides of said piston concentrically with said piston and said syringe; and a piston driving device coupled to an end of said piston rod to move said piston rod and said piston in either direction.

5. A fluid dispenser as recited in claim 4, wherein said stirrers are mounted on said piston rod so as to be able to rotate around and slide along said piston rod.

6. A fluid dispenser as recited in claim 5, wherein said stirrers are kept in the same axial positions in said syringe by the magnetic forces of said stirrer driving device, while said piston rod is being moved back and forth together with said piston.

7. A fluid dispenser as recited in claim 5, wherein each of said stirrers has a plurality of stirring blades on one end face thereof that is oriented away from said piston in said syringe.

8. A fluid dispenser as recited in claim 4, wherein said stirrers have a circular shape and are mounted in circular grooves that are provided around an inner peripheral portion of said syringe on either side of said piston, such that said stirrers are rotatable in said grooves around the piston rod.

9. A fluid dispenser as recited in claim 8, wherein each of said stirrers has a plurality of stirring blades on its inner periphery.

10. A fluid dispenser as recited in claim 4, wherein said syringe and said piston rod are oriented horizontally, and venting ports are provided through upper portions of the opposite ends of said syringe, said venting ports being able to open and close, wherein at the time of turning the moving direction of said piston, one of said venting ports that is on the side the liquid is just going to be dispensed from is turned open for a time immediately before the start of dispensing.

11. A fluid dispenser as recited in claim 10, wherein said one venting port is turned open while one of said ports that is on the same end of said syringe as said one venting port is still connected to said supply tank.

12. A fluid dispenser as recited in claim 10, wherein said piston is moved by a stroke while said one venting port is open, in a direction to dispense the liquid from said one port.

13. A fluid dispenser as recited in claim 10, wherein said syringe has large diameter sections on the opposite ends, and said venting ports are each located at a top portion of said large diameter section.

* * * * *